US009005151B2

(12) United States Patent
Lee

(10) Patent No.: US 9,005,151 B2
(45) Date of Patent: Apr. 14, 2015

(54) THERMAL APPARATUS

(76) Inventor: Choon Kee Lee, Denver, CO (US)

( * ) Notice: Subject to any disclaimer, the term of this patent is extended or adjusted under 35 U.S.C. 154(b) by 731 days.

(21) Appl. No.: 13/227,189

(22) Filed: Sep. 7, 2011

(65) Prior Publication Data

US 2013/0060185 A1 Mar. 7, 2013

(51) Int. Cl.
*A61N 2/12* (2006.01)
*A61M 1/36* (2006.01)
*A61N 1/40* (2006.01)
*A61M 5/44* (2006.01)

(52) U.S. Cl.
CPC ............. *A61N 1/406* (2013.01); *A61M 1/3693* (2013.01); *A61M 5/44* (2013.01)

(58) Field of Classification Search
CPC ....... A61M 1/36; A61M 25/00; A61M 25/10; A61N 1/08; A61N 2/00; A61N 2/02; A61N 2/12
USPC ................. 600/9, 12, 13, 109, 160, 549, 585; 607/96, 100–105, 113; 604/8, 96.01
See application file for complete search history.

(56) References Cited

U.S. PATENT DOCUMENTS

| | | |
|---|---|---|
| 4,752,141 A | 6/1988 | Sun |
| 4,979,518 A | 12/1990 | Itoh |
| 4,986,671 A | 1/1991 | Sun |
| 5,445,157 A | 8/1995 | Adachi |
| 5,571,153 A | 11/1996 | Wallsten |
| 5,632,764 A | 5/1997 | Beideman |
| 5,746,696 A | 5/1998 | Kondo |
| 5,793,268 A * | 8/1998 | Ataiiyan et al. ........... 333/219.2 |
| 5,873,817 A | 2/1999 | Kokish |
| 5,944,653 A | 8/1999 | Bonnell |

(Continued)

FOREIGN PATENT DOCUMENTS

| | | |
|---|---|---|
| DE | 2011058018 A2 | 5/2011 |
| DE | 2011101241 A1 | 8/2011 |

(Continued)

OTHER PUBLICATIONS

Hurst, G.C. et al. Intravascular (Catheter) NMR Receiver Probe:Preliminary Design Analysis and Application to Canine Iliofemoral Imaging. Magn Res Med (1992) 24: 343-357.*

(Continued)

*Primary Examiner* — Melanie Hand

(57) ABSTRACT

Provided herein are an apparatus and methods to induce electromagnetic field in biologic tissue for thermal therapy. The apparatus comprises electromagnetic devices fitted to be releasably deployed inside a body, magnetic materials to be deployed in a body, and a magnetic centrifuge machine. An electromagnetic device includes a controllably flexible fiberoptic tubular device with a magnetic-flux-controlled electromagnetic assembly on its distal end. The electromagnetic device receives direct or alternating electric current. Implanted particulate magnetic materials in close proximity to said electromagnetic assembly form reversible magnetic vascular mold in target blood vessels by static magnetic field produced by direct electric current to said electromagnetic assembly. Implanted magnetic materials generate heat by alternating magnetic field induced by alternating electric current to said electromagnetic assembly. A magnetic centrifuge machine removes magnetic materials from blood by centrifugation under static magnetic field after completion of thermal therapy.

24 Claims, 18 Drawing Sheets

(56) References Cited

U.S. PATENT DOCUMENTS

| | | |
|---|---|---|
| 5,995,875 A | 11/1999 | Blewett |
| 6,167,313 A | 12/2000 | Gray |
| 6,485,411 B1 | 11/2002 | Konstorum |
| 6,520,214 B1 | 2/2003 | Sugiyama |
| 6,599,234 B1 | 7/2003 | Gray |
| 6,623,424 B2 | 9/2003 | Hayakawa |
| 6,635,009 B2 | 10/2003 | Feucht |
| 6,668,197 B1 | 12/2003 | Habib |
| 6,673,104 B2 | 1/2004 | Barry |
| 6,702,846 B2 | 3/2004 | Mikus |
| 6,749,560 B1 | 6/2004 | Konstorum |
| 6,761,686 B2 | 7/2004 | Takase |
| 6,850,804 B2 | 2/2005 | Eggers |
| 6,895,282 B2 | 5/2005 | Gellman |
| 6,899,674 B2 | 5/2005 | Viebach |
| 7,048,756 B2 | 5/2006 | Eggers |
| 7,074,175 B2 | 7/2006 | Handy |
| 7,169,105 B2 | 1/2007 | Iwasaka |
| 7,174,217 B2 | 2/2007 | Rioux |
| 7,202,667 B2 | 4/2007 | Barbic |
| 7,252,680 B2 | 8/2007 | Freitag |
| 7,326,176 B2 | 2/2008 | Machiya |
| 7,513,876 B2 | 4/2009 | Casscells |
| 7,567,843 B2 | 7/2009 | Eggers |
| 7,579,550 B2 | 8/2009 | Dayton |
| 7,731,648 B2 | 6/2010 | Ivkov |
| 7,812,290 B2 | 10/2010 | Weber |
| 7,842,281 B2 | 11/2010 | Haik |
| 7,850,604 B2 | 12/2010 | Wimmer |
| 7,951,061 B2 | 5/2011 | Foreman |
| 7,967,839 B2 | 6/2011 | Flock |
| 2002/0133115 A1 | 9/2002 | Gordon |
| 2003/0032995 A1 | 2/2003 | Handy |
| 2003/0171691 A1* | 9/2003 | Casscells et al. ............ 600/549 |
| 2004/0104336 A1 | 6/2004 | Melnyk |
| 2004/0127895 A1 | 7/2004 | Flock |
| 2006/0009826 A1 | 1/2006 | Gleich |
| 2006/0030844 A1 | 2/2006 | Knight |
| 2007/0164250 A1 | 7/2007 | Hamad-Schifferli |
| 2007/0196281 A1 | 8/2007 | Jin |
| 2008/0221385 A1 | 9/2008 | Aulbach |
| 2008/0281386 A1 | 11/2008 | Herbette |
| 2009/0081122 A1 | 3/2009 | Rufenacht |
| 2009/0319010 A1 | 12/2009 | Hirayama |
| 2010/0099941 A1 | 4/2010 | Haik |
| 2010/0145420 A1 | 6/2010 | Zhu |
| 2010/0189157 A1 | 7/2010 | Saxena |
| 2010/0292564 A1 | 11/2010 | Cantillon Murphy |
| 2011/0034974 A1 | 2/2011 | Munoz Marquez |
| 2011/0052672 A1 | 3/2011 | Krishnan |
| 2011/0077451 A1 | 3/2011 | Marchitto |
| 2011/0151019 A1 | 6/2011 | Cheon |
| 2011/0190760 A1 | 8/2011 | Niver |

FOREIGN PATENT DOCUMENTS

| | | | |
|---|---|---|---|
| ES | 2009135970 A1 | 12/2009 | |
| ES | 2010066827 A1 | 6/2010 | |
| IT | 2008074804 A2 | 6/2008 | |
| JP | 2000079089 A | 3/2000 | |
| JP | 2001286436 A | 10/2001 | |
| JP | 2002345725 A | 12/2002 | |
| JP | 2004290351 A | 10/2004 | |
| JP | 2005137784 A | 6/2005 | |
| JP | 2005329188 A | 12/2005 | |
| JP | 2006055609 A | 3/2006 | |
| JP | 2009125457 A | 6/2009 | |
| JP | 2009233175 A | 10/2009 | |
| KR | 2010074539 A2 | 1/2010 | |
| KR | 2011055980 A2 | 5/2011 | |

OTHER PUBLICATIONS

Rata, M. et al. Endoluminal ultrasound applicator with an integrated RF coil for high-resolution magnetic resonance imaging-guided high-intensity contact ultrasound thermotherapy. Phys Med Biol (2008) 53: 6549-6567.*

Thomas et al., "Radiofrequency, microwave and laser ablation of pulmonary neoplasms: Clinical studies and technical considerations—Review article" European Journal of Radiology (2011) vol. 77, pp. 346-357, Elsevier, International.

Johannsen et al., "Magnetic nanopartide hyperthermia for prostate cancer" Int. J. Hyperthermia, (2010) vol. 26, No. 8, pp. 790-795, Informa Healthcare, International.

Sneed et al., "Survival benefit of hyperthermia in a prospective randomized trial of brachytherapy boost +/− hyperthermia for glioblastoma multiforme" Int J Radiat Oncol Biol Phys.(1998) vol. 40, No. 2, pp. 287-295, Elsevier, USA.

Deger et al., "Thermoradiotherapy Using Interstitial Self-Regulating Thermoseeds: An Intermediate Analysis of a Phase II Trial" European Urology (2004) vol. 45, pp. 574-580, Elsevier, Europe.

Jordan et al., "Inductive heating of ferrimagnetic particles and magnetic fluids: Physical evaluation of their potential for hyperthermia" Int J Hyperthermia. (2009) vol. 25, No. 7 pp. 499-511, Informa Healthcare, International.

Jordan et al., "Presentation of a new magnetic field therapy system for the treatment of human solid tumors with magnetic fluid hyperthermia" Journal of Magnetism and Magnetic Materials (2001) vol. 225, pp. 118-126, Elsevier, International.

Jordan et al., "Magnetic fluid hyperthermia (MFH): Cancer treatment with AC magnetic field induced excitation of biocompatible superparamagnetic nanoparticles" Journal of Magnetism and Magnetic Materials (1999) vol. 201, pp. 413-419, Elsevier, International.

Hilger et al., "Developments for the minimally invasive treatment of tumours by targeted magnetic heating" J. Phys.: Condens. Matter (2006) Suppl 18: pp. 2951-2958, IOP publishing, International.

Gupta et al., "Synthesis and surface engineering of iron oxide nanoparticles for biomedical applications" Biomaterials. (2005) vol. 26, No. 18, pp. 3995-4021, Elsevier, International.

Laurent et al., "Magnetic fluid hyperthermia: Focus on superparamagnetic iron oxide nanoparticles" Adv Colloid Interface Sci. (2011) vol. 166, No. 1-2, pp. 8-23, Elsevier, International.

Richter et al., "Magnetorelaxometry for localization and quantification of magnetic nanoparticles for thermal ablation studies" Phys. Med. Biol. (2010) vol. 55, pp. 623-633, IOP publishing, International.

* cited by examiner

THERMAL APPARATUS

STATEMENT REGARDING FEDERALLY SPONSORED RESEARCH OR DEVELOPMENT

The present invention is not a federally sponsored research or development.

TECHNICAL FIELD

The present invention relates generally to the field of treating tissue by high temperature. More specifically, the present invention provides an apparatus and methods to concentrate magnetic materials in a target area and to treat tissue of the target area in a lumen or a cavity of a body by heat energy induced by alternating magnetic field.

BACKGROUND OF THE INVENTION

Traditional ways in medicine to eliminate abnormal tissue or cells include surgery, chemotherapy, irradiation or combination of these. For radiation, both ionizing and non-ionizing types have been developed and successfully used for a range of abnormal tissues from overgrown blood vessels to pre-cancerous tissues to frank cancer. Ionizing radiation uses high energy particles enough to ionize atoms in a matter it passes through. It includes beta ray, x ray, gamma ray and neutron. Clinical application of ionizing radiation has been well developed to a point that it can be delivered to a specific area without damaging adjacent tissues, at a specific dose over a certain period of time to achieve a finite degree of tissue elimination in a consistent and reproducible way.

Thermal radiation belongs to non-ionizing radiation that includes infrared waves, microwaves and radiofrequency waves (Ref 1). Radiofrequency ablation uses resistive energy loss of tissue upon high frequency alternating electric current between 365 kHz and 550 kHz, delivered to longitudinal electrodes invasively inserted to a target tissue. Electric current passes from the longitudinal electrode to a electrically conductive pad attached to skin serving as a ground. The longitudinal electrode may have single or multiple probes and may be deployed through an introducer, as illustrated for an example in the U.S. Pat. Nos. 5,980,517 and 6,071,280. The generated resistive heat is proportionally dependent on the delivered radiofrequency energy and on intrinsic tissue properties such as heat conductivity and impedance. Drawbacks of the radiofrequency ablation include need of correct positioning of needle in the center of the target tissue, heat sink effect of adjacent blood vessels, small treatment volume, increasing impedance of the target tissue during therapy thereby progressively decreasing conductivity, inability to monitor temperature during therapy and occasional burn at a skin-to-ground transition site.

Microwave ablation operates between 915 MHz and 2.45 GHz, and electric field of microwave excites harmonic oscillations of water molecules in an alternating electric field. Other non-water molecules are heated by convection. Devices for microwave ablation comprise longitudinally insertable microwave antennas, as illustrated for an example in the U.S. Pat. Nos. 7,722,606 and 7,862,559, connected with a power and control unit via transmission cable. Microwave antenna emits electromagnetic radiation to tissue without an electric current, thereby avoiding problems of carbonization and tissue boiling. Compared to the radiofrequency ablation, microwave ablation may use multiple antennas at higher temperature covering a larger treatment volume without rising impedance. Yet temperature may not be monitored real-time during treatment. Size of a probe that houses antenna may be larger than that of radiofrequency probe, and selective heating of blood vessels may produce an increased risk of thrombosis of major blood vessels.

At near infrared, laser coagulation uses neodymium-yttrium aluminum garnet (Nd:YAG) laser light with a wavelength of 1064 nm. The laser produces monochromatic light and works independently of impedance rise that is associated with radiofrequency ablation. Success of laser coagulation depends on accurate delivery of laser optical fibers to a target area and real-time monitoring of therapy. Temperature may be monitored real-time and laser ablation may cover a larger treatment volume than radiofrequency ablation. Laser applicator is connected to a power and control unit via a coaxial sheath system, as illustrated in one example of the U.S. Pat. No. 7,344,529. Using a guidewire, a protective sheath should be positioned within or in the periphery of a target area before insertion of the laser applicator. The laser applicator needs to be inserted through the protective sheath to avoid direct contact with patient under computerized tomographic guidance. Ablation by laser then is monitored by magnetic resonance imaging. These multi-stage procedures increase chances of technical failure and also make the size of the sheath with applicator much larger than those of radiofrequency and of microwave ablation. Tissue carbonization may occur.

Hyperthermia with magnetic materials under alternating electromagnetic current was developed first in 1957 yet its widespread clinical use was hindered by technical limitations such as uncertain distribution of magnetic materials in a target area, need to place magnetic materials manually by needle injection or surgery, local tissue discomfort under high electromagnetic field strength due to the boundary effects, and difficulties in real-time monitoring of temperature and viability of the target area (Ref 2).

Despite these limitations, early clinical trials using thermoseeds of a pre-set Curie temperature embedded in tissue have been shown to be effective on enhancing killing of a few types of cancer such as brain cancer and prostate cancer, when used together with local radiation (Ref 3-4). Thermoseeds themselves could also retain radioactivity for combined potential for tissue ablation. For an example, the U.S. Pat. No. 6,497,647 proposes that cobalt combined with either palladum-103 or iodine-125 for ferromagnetic thermoseeds. These thermoseeds are usually paramagnetic, rod shaped and of millimeters in size. Main mechanism of heating of thermoseeds is Eddy current induced under alternating magnetic field that works on surface of the thermoseeds.

Further development of magnetic materials for hyperthermia produced multidomain ferromagnetic or ferrite particles, and ferromagnetic or superparamagnetic nanoparticles. Multidomain ferromagnetic particles are 1-300 μm in size and generate heat by a mechanism of hysteresis loss under alternating magnetic field. Ferromagnetic or superparamagnetic nanoparticles are 1-100 nm in size and generate heat mainly by Brownian and Neel relaxation processes (Ref. 5-6). Heating of a target tissue depends on specific absorption rate of an implanted magnetic material in an alternating magnetic field. Thermal energy is released to surrounding tissue as a result of physical processes that differ according to size of the magnetic material used and strength of the applied magnetic field (Ref 7). In an effort to enhance specificity to certain tissue, magnetic nanoparticles have been combined with antibody against tumor specific proteins such as Her-2/neu, and have been successfully localized to the target tissue (Ref 8). In another application, superparamagnetic iron oxide nanoparticles have been developed for hyperthermia albeit clinical benefit of hyperthermia using the iron oxide nanoparticles needs to be confirmed (Ref 9-10). Examples of these materials are described in the U.S. Pat. Nos. 6,541,039, 6,979,466, 7,074,175, 7,731,648, 7,842,281 and 7,951,061.

Hyperthermia by alternating magnetic field is limited by lack of specific localization of magnetic materials to a target area in a consistent and verifiable way; by need to introduce magnetic materials into a target area by surgery or direct injection oftentimes; by inhomogeneity of temperature distribution in the target area; by lack of real-time monitoring of temperature and effectiveness of tissue death; by nonspecific uptake of magnetic materials, especially of nanoparticles, by normal tissues of body such as macrophages and monocytes of the reticuloendothelial system, which may induce unwanted heating of normal tissues (Ref 11); by potentially high concentration of dissolved magnetic materials in blood such as iron oxide, which may cause toxicity; by the boundary effects by externally applied high strength magnetic field between tissues of different dielectric constant and conductivity (Ref 2); by increase in Eddy current density at skin level especially in folds under externally applied magnetic field (Ref 2); by lack of adequate means to deliver both alternating magnetic current and magnetic materials to a thin-walled body structure such as bowels, pleural or abdominal cavity.

SUMMARY OF THE INVENTION

The present invention describes an apparatus of devices and methods for thermal treatments of tissues associated with tubular or cavitary structure of a body in a reversibly localized way. A noble flexible fiberoptic tubular device is inserted into the body through natural openings and orifices or surgically created openings and channels. Said flexible tubular device provides static magnetic field to concentrate magnetically paired materials implanted in a target area or in target blood vessels of a target area, and provides alternating magnetic field to generate heat from said magnetically paired materials. Magnetically paired materials are particulate materials or thermal coils made of magnetic materials. Particulate magnetic materials are removed from the body by a magnetic centrifuge machine after completion of thermal treatments.

In one embodiment, the flexible tubular device has a proximal end and a distal end, and both the ends are connected via a controllably flexible tubular portion. There is provided a bending portion as part of the flexible tubular portion of said device, connected to the distal end. The proximal end of said device is connected to a power and control assembly. The distal end of said device comprises an electrically conductive coil in a plurality of configurations including at least a solenoid or an open toroid to form an electromagnetic assembly; one or a plurality of magnetic flux controllers; a plurality of heat tolerant and electromagnetic field tolerant fiberoptic cables; a plurality of temperature detectors of said electromagnetic assembly. The electrically conductive coil receives direct or alternating current from said power and control assembly.

In one embodiment, the distal end of said device may be configured as a longitudinal cylinder, a semicircle tube or a hollow tube to accommodate one or a plurality of configurations of the electromagnetic assembly. Said assembly in circular configurations around a longitudinal axis is housed in a longitudinally cylindrical distal end that emits circumferential electromagnetic field with the North and South of magnetic polarity located at both ends of said cylinder. Semicircle tube configurations have a longitudinally rectangular surface on one side of the tubular surface, along the axis of the distal end. Semicircle tube configurations of said assembly emits circumferential electromagnetic field with the North and South of magnetic polarity located at both axially longitudinal edges of the rectangle.

In one embodiment, one or a plurality of sizes and configurations of the electromagnetic assembly are chosen to optimize static or alternating magnetic field and vectorial distribution of magnetic field for geometry of said target blood vessels and said target area. Said electromagnetic assembly comprises said electrically conductive coil that winds up, in one or a plurality of configurations as a single continuous insulated wire, around magnetic flux controllers which are made of one or a plurality of ferrites or magnetodielectric materials. Magnetic flux of said assembly is controlled by one or a plurality of said ferrites or magnetodielectric materials, which has one or a plurality of permeabilities, saturation magnetic flux densities, resistivities and Curie temperatures. In another embodiment, magnetic flux control of said electromagnetic assembly is optimized by one or a plurality of numbers, sizes and configurations of the flux controlling ferrites or magnetodielectric materials.

In one embodiment, said electromagnetic assembly generates static magnetic field by direct electric current or alternating magnetic field by alternating electric current, supplied from said power and control assembly. In another embodiment, said power and control assembly provides said electromagnetic assembly with continuous direct electric current superimposed by on-off pulses of alternating electric current to first maintain attractive static magnetic force around the implanted magnetic materials by direct electric current and to secondly make said magnetic materials generate heat by pulses of alternating electric current.

In one embodiment, a plurality of fiberoptic cables of said device provide visual assessment and temperature monitoring of target area by infrared thermometry. Visual assessment and infrared thermometry are displayed real-time by a control module of said power and control assembly. A fiberoptic cable for visual assessment is connected distally to a forward looking fiberoptic view window on the side surface of said flexible tubular device close to or on the exterior of the distal end or at the front of the distal end. At said view window, said fiberoptic cable is connected to an optical lens complex that focuses and transmits light from said fiberoptic cable to the target area and receives returning light back to said fiberoptic cable. Said fiberoptic cable runs longitudinally along the axis of said flexible tubular device and is connected proximally to a view finder of the proximal end of said device and to the power and control modules. A dedicated fiberoptic cable for infrared thermometry runs in parallel with said fiberoptic cable for temperature assessment from the view window to the power and control module. Infrared fiberoptic cable is also connected at the view window to an optical lens complex that transmits infrared light from said infrared fiberoptic cable to said target area and receives said returning light back to said infrared cable. The control module displays temperature information in digitized numerical format.

In another embodiment, a second dedicated fiberoptic cable for infrared thermometry is connected at a forward looking fiberoptic view window to an optical lens complex provided at the front of the distal end of said device. Said fiberoptic cable runs longitudinally along the axis of said flexible tubular device and is connected to said power and control modules. The first fiberoptic cable gathers information on infrared thermometry of a target area and the second fiberoptic cable on infrared thermometry of a non-target area. Temperature differences between the target area and the non-target area under therapy are monitored by the control module that receives information on temperature from two said fiberoptic cables of said device simultaneously.

In yet another embodiment, both fiberoptic cables for visual assessment and for infrared thermometry are combined as one bundle of cables that run longitudinally along the axis of said flexible tubular device, and is connected proximally to a view finder of the proximal end of said device and to the power and control modules and distally to a forward looking fiberoptic view window on the side surface of said flexible tubular device close to or on the exterior of the distal end or at the front of the distal end.

Optical fibers comprise materials made of silicate glass and a few metallic materials as dopant to adjust refractive index. Optical fibers for infrared range comprise chalcogenide glass, chalcohalide glass, fluoride glass, zinc selenide, germanium or silicon. The optical fibers are protected by outer sheath. Although silicate glass has a wide range of heat tolerance, chalcogenide or chalcohalide glass has limited temperature tolerance. Chalcogenide or chalcohalide glass tolerates temperature up to 80° C. before it begins to get softened. Presence of non-diamagnetic metallic materials as dopant in optical fibers would adversely affect performance and physical conditions of the optical fibers under electromagnetic field. The protective sheath, made of polymers, has a wide range of temperature tolerance, depending on types of polymers.

In one embodiment, optical fibers of the flexible tubular device of the present invention comprise silicate glass mixture of silicon dioxide and germanium dioxide to achieve a range of temperature tolerance up to 350° C. and without non-diamagnetic metallic dopants to eliminate electromagnetic influence on said optical fibers by said electromagnetic field generated by said electromagnetic assembly. Examples of non-diamagnetic metallic dopants are, but not limited to, titanium, chromium, erbium, or aluminium. The optical lens complex of said view window for said optical fibers for visual assessment comprises silicon dioxide, zinc selenide, germanium dioxide or fused quartz, to increase heat tolerance and to eliminate electromagnetic influence.

In one embodiment, the optical fibers for infrared thermometry of said flexible tubular device comprise chalcogenide, chalcohalide, zinc selenide, germanium or silicon, without non-diamagnetic metallic dopants. The optical lens complex of said view window for infrared optical fibers comprises germanium dioxide, zinc selenide or silicon, which are known for high temperature tolerance and are diamagnetic.

In another embodiment, infrared optical fibers of chalcogenide or chalcohalide glass are to be used in conjunction with the types of distal end that has water cooling system to prevent material failure on high temperature. In another embodiment, said sheath comprises one or a plurality of heat resistant and elastic polymers. One example of said polymers comprise polyimide materials.

In one embodiment, the distal end of said device may have one or a plurality of cooling systems using water which is provided by said power and control assembly of said device via flexible tubular conduits. One example of said cooling system comprises a cooling chamber longitudinally disposed about said electromagnetic assembly along the axis, which is connected to at least two separate water conduits with each said conduit supplying and suctioning off cooling water, respectively. Said conduits run longitudinally along the axis of said device from said power and control assembly to said cooling chamber. Said conduits have a plurality of holes thereof inside the cooling chamber, with said holes of a water inflow conduit located close the front of the cooling chamber and said holes of a water outflow conduit located close to the back of said chamber.

In one embodiment, water is pumped into said cooling chamber in one or a plurality of methods by said power and control assembly. Temperature of said electromagnetic assembly is monitored by said control module of said power and control assembly for differences in the temperature between inflow and outflow of water of said cooling system. Said cooling system circulates water between said distal end and a heat exchange unit of said power and control assembly to maintain temperature of said distal end below tissue damaging temperatures.

In another embodiment, the water cooling system is omitted to reduce size and weight of the distal end of flexible tubular device. Decrease in the size of the distal end allows said flexible tubular device to be inserted to narrowly confined areas or obstructed areas. Electromagnetic assembly of said distal end comprises one or a plurality of rod shaped or hollow tubular shaped magnetic flux controllers and electrically conductive coil wound around said magnetic-flux-controllers. Said hollow tubular space of said distal end serves as conduit for water, air, guidewire, magnetic thermal coil, or other materials to be delivered to a target area.

In one embodiment, an electromagnetic assembly without the water cooling system has one or a plurality of resistant temperature detectors that are attached to the surface of said electrically conductive coil of said assembly. Said detectors are connected to said power and control assembly via electrically conductive wires that run longitudinally along the axis of said device. Temperature of said electromagnetic assembly is monitored by the control module that regulates electricity to said electromagnetic assembly to maintain operable range of temperature of said electromagnetic assembly.

In one embodiment, the distal end of said flexible tubular device may have one or a plurality of position stabilizing systems. Said system comprises at least one air balloon longitudinally attached along the axis of said device to a part of the outer circular surface of the distal end of said device. Said air balloon receives pressured air from said power and control assembly via a conduit that runs inside said flexible tubular device, longitudinally along the axis of said device. When the distal end of said device is placed in a lumen or a cavity of a body, which is larger than said distal end of said device, said balloon is expanded by air insufflation through said conduit to fill up a space between said distal end of said device and said lumen or said cavity. The expanded balloon immobilizes said distal end as said space is filled up without a remaining space in which said distal end may move.

The electromagnetic assembly of the distal end of said device increases overall weight that hinders accurate navigation of said device in the body. In one embodiment, the bending portion of said flexible tubular device has a spirally wound tubular shaft longitudinally placed along the axis of said device for a range of length, an outer spiral ribbon that encircles said spirally wound tubular shaft, a bending cable attachment portion located at a joint between said distal end of said device and said bending portion, and a plurality of bending cables connecting said attachment portion to bending control knobs at said proximal end of said device. Said spirally wound tubular shaft and said spiral ribbon are part of outer wall complex of said device. Said joint comprises an internal helical fastener that connects a proximal part of said distal end to said bending portion of said flexible tubular device. Said spirally wound tubular shaft has one or a plurality of cylindrical helix configurations and is connected to said internal helical fastener of said joint. Each spiral of said spirally wound tubular shaft overlaps an adjacent spiral for a range of length in a number of ways that there always is an enfolding overlap between two spirals facing each other over one or a plurality of bending radii of said spirally wound tubular shaft to spread the weight of said distal end over the length of said tubular shaft. Said spirally wound tubular shaft has a plurality of pitches between two enfolding helical edges to accommodate a range of bending radii.

In another embodiment, said spiral ribbon is connected to said internal helical fastener of said joint outside of said spirally wound tubular shaft. Said spiral ribbon runs inside said flexible tubular device, longitudinally along the axis, and is connected to a knob located at the proximal end of said device. Said spiral ribbon helically is disposed about said spirally wound tubular shaft, wherein a diameter of said spiral ribbon in a neutral position is larger than that of said spirally wound tubular shaft. When said spiral ribbon is pulled by said knob toward the proximal end of said flexible tubular device, the diameter shrinks and fastens said spirally wound tubular shaft, thereby immobilizing it.

In one embodiment, said flexible tubular device has one or a plurality of conduits to deliver a guidewire, thermal coils, catheters, water or air or to provide electrically conductive wires or temperature detectors from said power and control assembly or from said proximal end to said distal end. Said conduits run longitudinally along the axis of said device from said proximal end or from the power and control assembly to said distal end. At the proximal end of said device, said conduits are connected to a source of air or water or to ports for introduction of said guidewire, thermal coils or catheters. Said electrically conductive wires and said temperature detectors are connected to said said power and control assembly. Said power and control assembly also provides said distal end with pressured air and pressured water for cooling through said heat exchange unit.

In one embodiment, said flexible tubular device and the implanted magnetic materials are placed close to each other to be electromagnetically paired. Said magnetic materials comprise at least one magnetic metal or an alloy of a plurality of different metals. Particulate magnetic materials may range from 1 nm to a few hundreds micrometers in size and may be ferromagnetic, paramagnetic or superparamagnetic. In one embodiment, said magnetic materials may have one or a plurality of configurations, which are suspended in fluid of one or a plurality of solutions and in one or a plurality of concentrations. Said fluid is to be introduced to target blood vessels and to a target area by selective catheterization of arteries supplying blood to or of veins draining blood toward the target tissue.

Said fluid containing magnetic particles exhibit changes in viscosity off and on static electromagnetic field. Said fluid containing magnetic particles is in liquid phase and its viscosity is low in its natural condition without static electromagnetic field around said fluid. Off static electromagnetic field, said magnetic particles in said fluid fall to the lowest gravitational level by weight of said magnetic particles unless there is Brownian force applied to said particles in a confined system of blood vessels and constant blood flow through the vessels. Once static electromagnetic field is applied to said fluid, magnetic particles align themselves along magnetic flux lines of electromagnetic field, form reversible, magnetically randomly linked lattice structure of said magnetic particles, thereby increasing viscosity to gel-like or semi-solid consistency. Flow characteristics of blood or materials of liquid in nature through said gel-like phase of said fluid in part depends on shear strength of said magnetic particles and said fluid. This nature of change in phase of said fluid between liquid and gel-like (or semi-solid) is defined as 'transphasic' in the present invention.

In another embodiment, magnetic particles of different sizes and shapes are combined together at varying ratios to optimize one or a plurality of shear strengths and particle sedimentations of magnetorheological property of said transphasic fluid containing a range of concentrations of said magnetic particles off and on static electromagnetic field. Induction of gel-like phase of said transphasic fluid helps keep in place magnetically reversibly molded mass of said magnetic particles in the target blood vessels and at the target area without random dispersion, and facilitates transfer of heat energy from said magnetic particles by alternating electromagnetic field to said target blood vessels and said target area. One example of combination is to mix sphere shaped particles with elliptical-rod shaped particles in varying ratios. Following completion of thermal treatment, turning off electromagnetic field allows said gel-like phase of transphasic fluid containing said magnetic particles to revert back to said liquid phase of low viscosity with randomly dispersed individual magnetic particles that flow to systemic circulation.

There are a plurality of methods of localization of said magnetic materials to a target area by vascular catheterization. In one embodiment, one or a plurality of preset levels of static magnetic field of said electromagnetic assembly produced by one or a plurality of direct electric currents are calibrated by magnetometer for its vectorial field strength and magnetic volume according to a plurality of volumes of a target area before insertion of said flexible tubular device into a lumen or a cavity. Following calibration, said flexible tubular device is introduced into the target area of the lumen or the cavity and stabilized for its position. After confirming the location, a preset static magnetic field for the target area is generated by direct electric current to said electromagnetic assembly of said device. After confirming proper operation of said electromagnetic assembly, electricity to said assembly is turned off while patient undergoes vascular catheterization.

For vascular catheterization, in one embodiment, patient will be placed under x-ray fluoroscopy to visually guide a vascular catheter to a target vessel that supplies blood to or drains blood from a target area. Said vascular catheter is introduced to said target vessel through one of suitable blood vessels by one or a plurality of techniques. Once the tip of said catheter is lodged in said target vessel, said electromagnetic assembly of said device inside the body receives direct electric current and generates a static magnetic field continuously for a range of length of time. While said static magnetic field is maintained on, a volume of saline of varying concentrations is rapidly injected as a bolus to flush out blood in the target blood vessels. Immediately following the saline flush, a test dose of one or a plurality of preset amounts of radiographically visible magnetic particles in transphasic fluid is injected to said target vessel through said catheter. Confirmation of localization of said test dose of magnetic materials to said target area is done radiographically.

Following the confirmation of localization of said magnetic materials, a full treatment dose of one or a plurality of preset amounts of said transphasic fluid containing said magnetic particles is injected to said target blood vessels and said target area over a preset range of length of time, again immediately preceded by second bolus injection of saline to flush out blood. After completion of full injection of said transphasic fluid through said catheter, saline of temperature higher than normal body's temperature by a few degrees centigrade, for an example, in between of 38° C. and 39° C., continues to be infused at a range of infusion rates through said catheter until completion of thermal treatment. Following completion of thermal treatment, temperature of saline for infusion drops to a few degrees centigrade, for an example, between 34° C. and 36° C., for cool-down process.

Continuous infusion of warm saline during thermal treatment is first to prevent localized intravascular coagulation and thrombosis of blood mixed with said transphasic fluid under electromagnetic heating, both of which could be serious consequences of heating of blood and secondly to prevent loss of heat energy from said magnetic materials under alternating electromagnetic field by circulating blood of normal body temperature in between of 36.5° C. and 37.5° C.

In another embodiment, after completion of injection of said full treatment dose to said target area, while said catheter continues to infuse saline, said direct electric current to said electromagnetic assembly is changed to one or a plurality of alternating currents or to one or a plurality of combinations of one or a plurality of continuous direct electric currents superimposed by one or a plurality of on-off pulses of alternating electric currents. Said electromagnetic assembly generates alternating electromagnetic field in and around said magnetic materials by said alternating electric current. Said magnetic particles adhere to each other by magnetic attraction under static electromagnetic field, thereby forming a reversible internal mold of the blood vessels made of random magnetic lattice-like structure suspended in said transphasic fluid. Under alternating electromagnetic field, individual particles of small size that produce heat energy by hysteresis loss, Brownian or Néel relaxation processes and said internal magnetic mold of said lattice-like structure inside said blood vessels produces heat energy by one or a plurality of combinations of Eddy current, hysteresis loss, Brownian or Néel relaxation processes.

In one embodiment, following completion of the hyperthermia of said target area and said target blood vessels, said alternating electric current to said electromagnetic assembly is changed to direct electric current for a range of length of time to maintain said static electromagnetic field to keep said gel-like fluid with magnetic particles in place in said blood vessels and at said target area during a cool-down process of said magnetic materials. Said cool-down process is achieved mainly by saline of low temperature infused through said catheter and of a smaller magnitude by blood of normal body temperature, which flow through said magnetic materials in the absence of alternating electromagnetic field. Duration of said cool-down process may be predetermined by said preset amount of treatment dose of magnetic materials and by the duration and intensity of said alternating electromagnetic field. In another embodiment, said duration of said cool-down process may be calculated by one or a plurality of nomograms constructed by a range of amounts of treatment dose of magnetic materials, a range of duration and intensity of alternating electromagnetic field and a range of volume of the target area.

In one embodiment, said magnetic materials that were delivered to said target vessels by said vascular catheterization are releasably retrieved from blood circulation after withdrawal of said electromagnetic assembly from a body following completion of the hyperthermia and cool-down process. One or a plurality of closed systems of magnetic centrifuge machine having one or a plurality of operating devices have a rotating chamber that receives and spins blood therein, one or a plurality of fixed static magnets outside said rotating chamber in close proximity to a wall of said chamber, a rotor that receives electricity and rotates said chamber, a blood inflow conduit and a blood outflow conduit, both connecting said chamber of said machine to patient, a control module of said machine and a housing of said machine.

Said magnets are permanent magnet or electromagnet that receives direct electric current, which produces static magnetic field in and around said chamber. Said blood inflow conduit is connected to a blood vessel of patient and delivers blood to said chamber. Said chamber spins blood in one or a plurality of methods, to separate said magnetic materials from the rest of blood by differences in weight and density and by magnetic gravitation. Separated said magnetic materials are localized to a surface of an inner wall of said chamber by magnetic gravitation to said magnets around said chamber, while the rest of blood returns back to patient via said blood outflow conduit connected to other blood vessel of said patient. After completion of said separation process, said magnetic materials in said chamber are discarded.

In one embodiment, magnetic materials form linear strings, which may range from a few hundreds micrometers to a few millimeters in diameter and may be ferromagnetic or paramagnetic. Said strings of magnetic materials may have one or a plurality of linear or cylindrically helical configurations, which form expandable thermal coils and are to be releasably deployed in a lumen or a cavity. Thermal coil is to generate and deliver heat energy to target tissue for hyperthermic therapy under alternating electromagnetic field. Abnormal tissues of the target area die of thermal injury delivered by said thermal coil.

In one embodiment, one or a plurality of thermal coils made of magnetic thermal materials are introduced into a lumen or a cavity by one or a plurality of methods. Thermal material comprises one or a plurality of alloys, which exhibits changeable expansile tensile strength and elasticity over a range of temperature. Thermal coil is shaped as cylindrically helical longitudinally along the axis and its axial cross-sectional diameter can be variable upon divergent diameters of said lumen of cavity.

Preferably said thermal coil is constructed in two parts combined longitudinally along said coil, with one part located outside of helical cylinder of said thermal coil and the other part located inside of said cylinder of said thermal coil. Said part located outside contacts tissues of said lumen or said cavity and said part located inside faces luminal part of said lumen or empty space of said cavity. Said part located outside comprises one or a plurality of thermal materials and said part located inside comprises one or a plurality of thermal barrier polymers encasing part of said thermal materials. Said thermal barrier reduces convection of heat energy of said thermal material to air and water inside said lumen or said cavity, and directs said heat energy only to said tissues of said target area in contact.

One embodiment of methods of introduction is to thread one or a plurality of linear thermal coils through a conduit of said flexible tubular device to a target area under direct vision via a fiberoptic cable of said device. During transit through said distal end of said device, said thermal coil gets heated up by alternating electromagnetic field generated by said electromagnetic assembly of said distal end. Austenite state on high temperature induces one or a plurality of cylindrical helical coil shapes whereas martensite state on low temperature maintains one or a plurality of linear shapes of thermal coil. Expanded thermal coil in one or a plurality of helical configurations then is deployed inside a lumen of a target area, abutting on inner wall of said lumen. Said distal end is longitudinally placed inside said expanded thermal coil and generates alternating electromagnetic field. Said thermal coil generates heat by Eddy current upon said alternating magnetic field, which transfers heat energy mainly by conduction to said target area.

Another embodiment of methods of introduction is to deliver said thermal coil over said flexible tubular device into a lumen or a cavity under alternating electromagnetic field of a strength enough to deploy said thermal coil by thermal change from martensite state to austenite state of said thermal coil, with said thermal coil located on the exterior of the distal end of said device in one or a plurality of methods and configurations. After introduction of said thermal coil into said target area and full expansion of said thermal coil, said electromagnetic assembly of said device, deployed inside said thermal coil, generates alternating magnetic field by alternating electric current for treatment.

In one embodiment, said thermal coil is releasably removed following completion of hyperthermia by one or a plurality of methods. In another embodiment, said thermal coil may be left in place inside said lumen or said cavity for repeat hyperthermia. In yet another embodiment, one or a plurality of conventional intraluminal stents may be placed in at the site of hyperthermia following removal of said thermal coil, to maintain structural support of said target area.

In one embodiment, the goal of hyperthermia by the present invention is to achieve temperature of a target area high enough to make tissue of said target area die but low enough to avoid damage to normal tissue adjacent to said target area over a range of duration, which is between 42° C.~45° C. of said target area. When temperature differences between a non-target area and target area under therapy are monitored, the goal of said temperature differences is to achieve 6° C.~8° C. higher temperature at the target area under therapy.

In another embodiment, the present invention induces death of target blood vessels connected to said target area. Said transphasic fluid of said magnetic particles, introduced into said target blood vessels, forms said gel-like fluid under electromagnetic field. Said particles in said gel-like fluid filled up inside said target blood vessels act as internal mold of said target blood vessels. Said particles in said gel-like fluid in direct contact with tissues of wall of said blood vessels transfer heat energy under alternating electromagnetic field to said tissues, thereby inducing death of said tissues of said blood vessels.

The hyperthermia by the present invention has one or a plurality of durations, intensities and volumes of alternating magnetic field to optimize killing of abnormal tissue. Said hyperthermia is driven by said power and control assembly that has one or a plurality of methods to provide said flexible tubular device with electricity, infrared and visible lights and substances, and heat exchanges. Said control module provides control of said flexible tubular device and the target area.

Metallic materials having any magnetic property, if paired electromagnetically, will be affected by the electromagnetic field produced by the electromagnetic assembly of the flexible fiberoptic tubular device. Said metallic materials may generate electromagnetic energy that may interfere with functions of mechanical and electronic components of said flexible fiberoptic tubular device. Therefore it is necessary to avoid use of metallic materials for one or a plurality of parts of said flexible fiberoptic tubular device, other than for the plurality of components described above for the electromagnetic assembly, electrically conductive wires and temperature detectors.

In one embodiment, a plurality of components of said distal end, except for said electromagnetic assembly, electrically conductive coil and wires and resistant temperature detectors, and of parts of said flexible tubular portion of said flexible fiberoptic tubular device are made of heat resistant polymers without metallic materials, which have a range of structural strength and a range of elasticity to avoid the mechanical interference from said electromagnetic field produced by said electromagnetic assembly. Electronic components of said flexible fiberoptic tubular device and the power and control assembly are properly shielded from said electromagnetic field by one or a plurality of methods. One embodiment of said methods includes thin-layer copper coating on inner wall of enclosure of said power and control assembly. Another embodiment includes bendable mesh of thin braided copper wires disposed about a plurality of components of tubular or cylindrical structure.

BRIEF DESCRIPTION OF THE DRAWINGS

Overview shows a schematic explanatory summary of the present invention.

DETAILED DESCRIPTION OF THE DRAWINGS

As described below, the present invention provides a number of devices and methods of use. It is to be understood that the descriptions are solely for the purposes of illustrating the present invention, and should not be understood in any way as restrictive or limited. Embodiments of the present invention are preferably depicted with reference to FIGS. 1 to 18, however, such reference is not intended to limit the present invention in any manner. The drawings do not represent actual dimension of devices, but illustrate the principles of the present invention.

The overview illustrates a schematic overview of an example of placement of a flexible tubular device A with an electromagnetic assembly of a distal end in a lumen of an intestine via a fiberoptic system B, and of a central vascular catheter C in one branch of arteries leading up to a target area. The flexible fiberoptic tubular device is connected to a power and control assembly D. The flexible tubular device A is guided into the lumen and positioned to the target area under visual guidance by an operator using the fiberoptic system B. The central intravascular catheter C is introduced into the target blood vessel under x-ray fluoroscopy. The power and control assembly D provides electricity to the device A, thereby generating electromagnetic field in and around the distal end of the device A. Magnetic materials are injected into the target area through the catheter C and get concentrated to the target blood vessels and to the target area under a direct magnetic field produced by direct electric current to the electromagnetic assembly of the distal end of the device A. Following concentration, said magnetic materials generate heat by alternating magnetic field produced by an alternating electric current to said electromagnetic assembly of the distal end of the device A.

Figure 1:
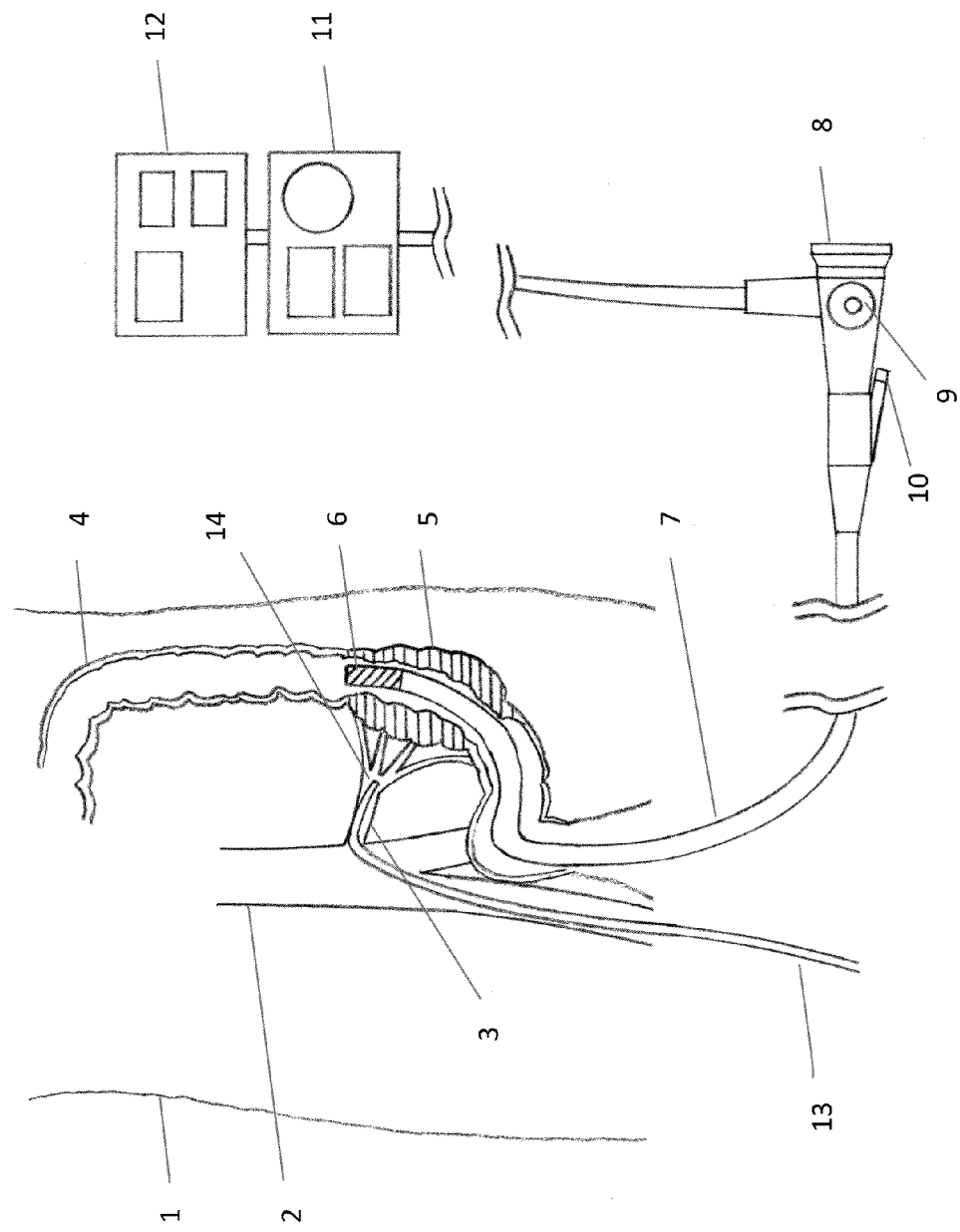
FIG. 1 shows itemized components of the overview.

Referring to the overview, FIG. 1 depicts individual components of the schematic overview of hyperthermic therapy by the present invention. In a trunk 1 of a body, there are a descending aorta 2 with its inferior mesenteric artery branch 3, a descending colon 4 and a colon cancer 5. Distal end 6 of a flexible tubular device 7 is flexibly guided into a lumen surrounded by the colon cancer 5 by an operator who uses a fiberoptic viewfinder located at proximal end 8 of the device 7 and control knobs 9 of the proximal end 8 of the device 7 to navigate the device 7. The proximal end 8 is connected to both control module 11 and power module 12 to receive electricity, infrared and visible lights, air and water. The control module 11 monitors and regulates electricity of said power module 12, monitors and regulates temperature of the target area 5 via the fiberoptic system and of said distal end 6, visually monitors said target area and monitors and regulates air provided to said distal end 6. Port 10 is connected to conduit inside the flexible tubular device 7 and is to deliver air, water, catheter or thermal coil.

Once the distal end 6 is in place at the target area, a catheter 13 is introduced into the aorta 2 under x-ray fluoroscopy, with its tip 14 inserted into the inferior mesenteric artery 3. Transphasic fluid with magnetic materials are then injected through the catheter 13 into blood vessels that lead to the target area 5, while the control module 11 supplies direct electric current to the distal end 6 thereby generating a direct electromagnetic field around the target area 5. Once the magnetic materials are in place at the target area 5, the control module 11 provides alternating electric current to the distal end 6 that in turn generates an alternating magnetic field around the target area 5. The magnetic materials in the blood vessels of the target area 5 generate heat under the alternating magnetic field.

Figure 2:
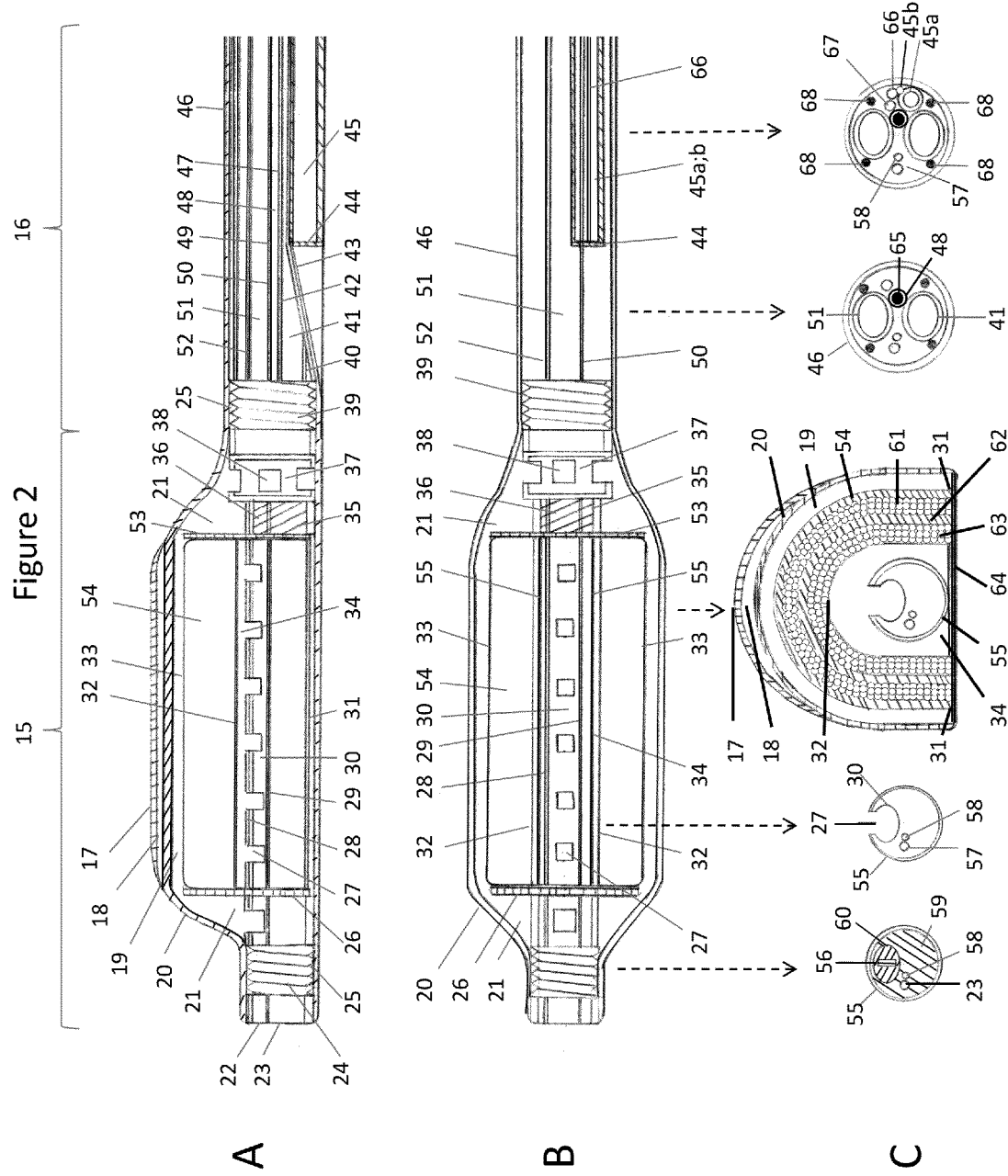
FIG. 2 illustrates a schematic view of an example of a distal end and a part of a tubular shaft of Type A flexible tubular device.
Figure 3:
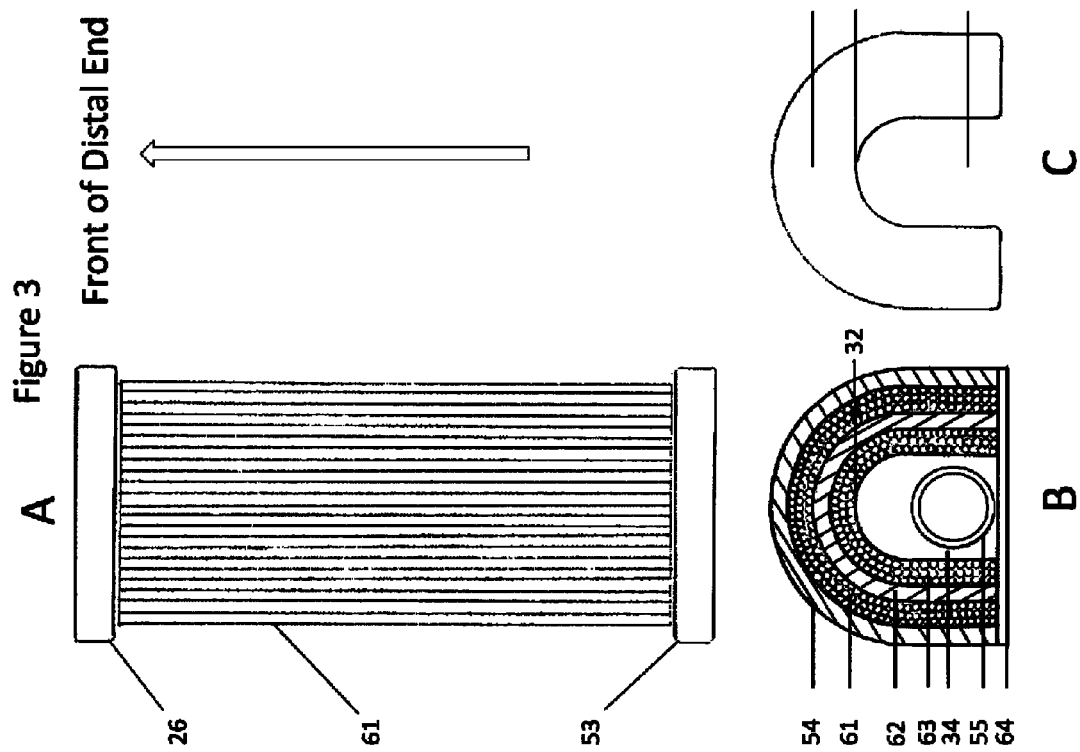
FIG. 3 shows a schematic view of an example of a wound coil and magnetic flux controllers of an electromagnetic assembly with its outer longitudinal magnetic flux controller removed.
Figure 4:
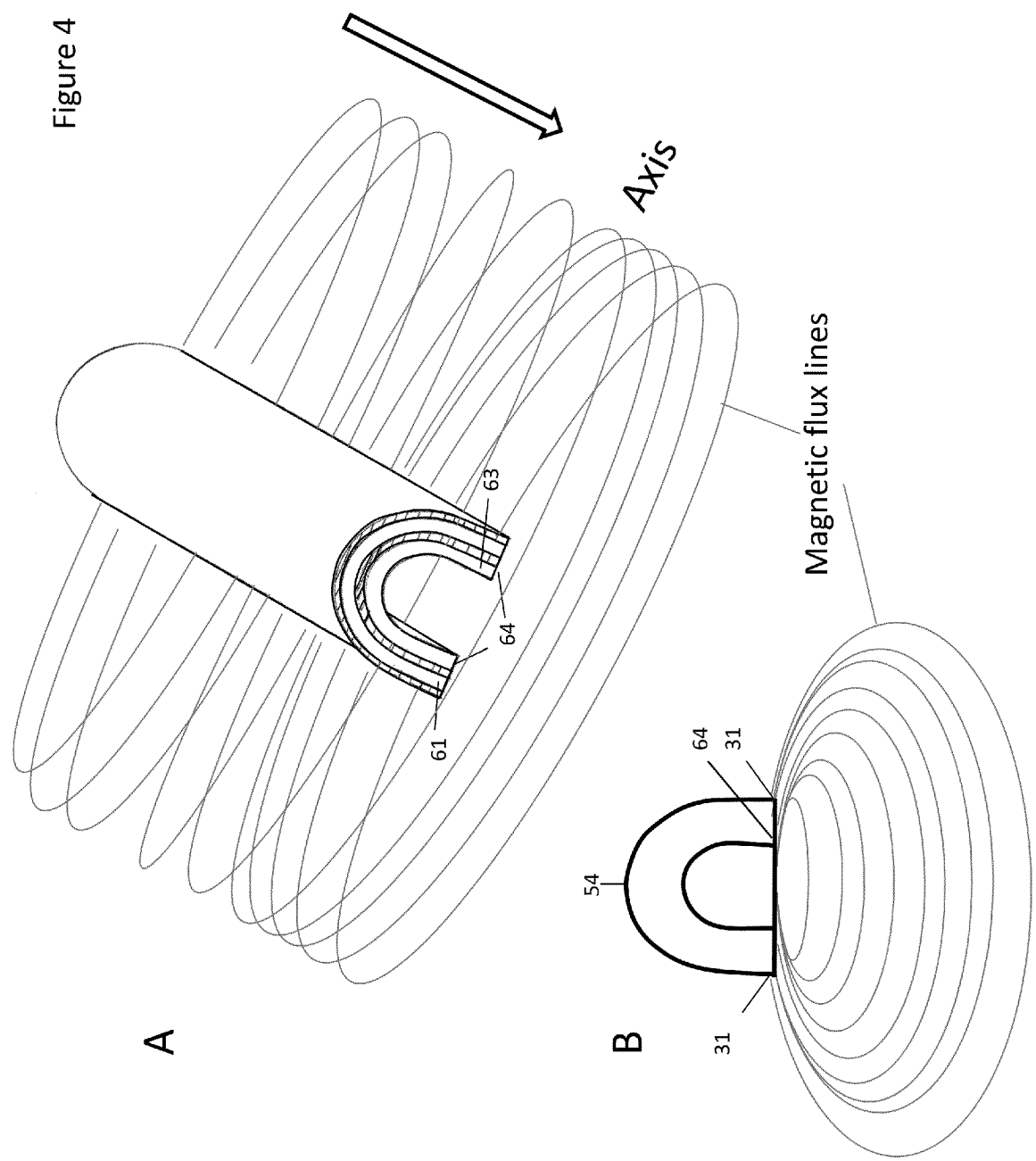
FIG. 4 shows a schematic view of an example of an electromagnetic assembly with both of its ends exposed and of distribution of magnetic flux of electromagnetic field.

FIG. 2 shows a schematic view of an example of distal end 15 and a part of bending portion 16 of Type A flexible fiberoptic tubular device. FIG. 2A shows a side view of said device; 2B a top-down view; 2C cross-sectional views. The distal end 15 is surrounded by enclosure 20 and is tightened by internal helical fasteners 24 and 39 on its front and back ends. Portion of outer wall of the enclosure 20 corresponding to the internal helical fasteners is designated as 25. The enclosure 20 is made of one or a plurality of heat resistant polymers that have a range of thermal tolerance beyond maximum temperature produced by electromagnetic assembly 33. On the semicircular surface of the enclosure 20, air balloon 17 with its ballooning space 18 is attached longitudinally along the axis of the distal end 15. Air conduit 67 connects the air balloon 17 to the power and control assembly 11 and 12 as shown in FIG. 1, which provides pressured air to inflate the air balloon 17.

The enclosure 20 surrounds the electromagnetic assembly 33 along with its magnetic flux controllers 26 and 53 on its front and back ends, internal tube 55 that houses water inflow conduit 30 and infrared fiberoptic cable 57 with its accompanying water washer conduit 58, and water outflow hub 37.

The electromagnetic assembly 33 comprises inner magnetic flux controller 62, electrically conductive coil 61 as a single wire continuously wound longitudinally along the axis around the inner magnetic flux controller 62 to become coil 63 on a cross sectional view, outer magnetic flux controller 54 covering the wound coil 61, and magnetic flux controllers 26 and 53 on its front and back ends. The wound coil of single wire 61 & 63 receives electricity from the power and control assembly 11 and 12 as shown in FIG. 1 via electrically conductive wire 65. The electrically conductive coil 61 & 63 and wire 65 are insulated by heat resistant polymers. The electric conductive wire 65 runs longitudinally inside insulated conduit 48. The insulated conduit 48 is bordered by wall 47 and 49.

Magnetic flux controllers 26, 53, 54 and 62 are to amplify and concentrate magnetic field on and around bottom 64 along the length of the distal end 15. North and south poles of magnetic field are formed on the bottom 64 on its longitudinal edges 31 along the axis of the assembly 33. The bottom 64 is directed toward and to contact a target area to be paired with the magnetic materials.

Inside the enclosure 20, there are areas of space for water circulation that is used for cooling of the assembly 33. Space 19 surrounds the outer magnetic flux controller 54, space 21 is located outside the magnetic flux controllers 26 and 53 and space 34 is located inside inner wall 32 of the assembly 33. Water flows into the enclosure 20 via the inflow conduit 30 that is bordered by wall 28 and 29. There are a plurality of holes 27 on the upper surface of the water inflow conduit 30, through which water gets into the areas of space 19, 21 and 34 inside the enclosure 20.

The water inflow conduit 30 is connected to main water inflow conduit 51 through the water outflow hub 37 and gap seal 35 that is located between the water outflow hub 37 and the inner space 34. The portion of the water inflow conduit in the gap seal 35 is designated as 36. The gap seal blocks off communication between the water outflow hub 37 and the inner space 34. The main water inflow conduit 51 is bordered by wall 50 and 52 and runs longitudinally inside the Type A flexible tubular device. The main water inflow conduit 51 bifurcates before the proximal end 8 as shown in FIG. 1 to a water conduit connected to the power and control modules 11 and 12 as shown in FIG. 1 and to a conduit connected to the port 10. The power and control modules 11 and 12 supplies pressured water for circulation.

The water outflow hub 37 has a plurality of holes 38 on its side wall and is connected to main water outflow conduit 41. The main water outflow conduit 41 is bordered by wall 40 and 42 and runs longitudinally inside the Type A flexible tubular device to the power and control modules 11 and 12 as shown in FIG. 1, where it receives negative pressure suctioning.

Water supplied by the power and control modules 11 and 12 as shown in FIG. 1 flows through the main inflow conduit 51, circulates in the areas of space 34, 21 and 19 inside the enclosure 20, and is suctioned off through the water outflow hub 37 and returns to the power and control modules 11 and 12 through the main outflow conduit 41. The power and control modules 11 and 12 measure temperature of both inflow and outflow of water and regulate volume, speed and temperature of circulating water to cool down the electromagnetic assembly 33 to preset operating temperature. The power and control modules 11 and 12 have a heat exchange unit for circulating water.

The water inflow conduit 30 continues on to the front 22 of the internal tube 55 and terminates. The termination front 22 comprises viscoelastic seal 60 and slit 56 in the middle of 60. The viscoelastic seal 60 and slit 56 run for a range of length inside the internal tube 55. The termination front 22 of the internal tube 55 has seal 59 for a range of length inside the internal tube 55. The slit 56 is close shut under normal circumstances but is to reversibly widen to accommodate a longitudinal catheter or thermal coil for deployment into a target area. The port 10 is connected to the main water inflow conduit 51 via the bifurcation near the proximal end 8 as shown in FIG. 1 and has one-way check valves that prevent regurgitation of pressured water from the water inflow conduit 51. Catheter or thermal coil is to be introduced through the port 10, advances inside the water inflow conduit 51 and protrudes from the slit 56 for deployment into a target area. Water circulation for cooling is held during the placement of catheter or thermal coil.

The fiberoptic cable 57 is connected distally to view window 23 located at the front of the internal tube 55 and runs longitudinally along the axis to the power and control modules 11 and 12, as shown in FIG. 1, which provide infrared light. The fiberoptic cable 57 is to measure temperature of tissue by infrared thermometry. Main forward looking fiberoptic cable complex 45 is located in the bending portion 16, exposed to the side of the exterior thereof, with its view window 44 faced forward. The fiberoptic complex 45 comprises fiberoptic cable 45a for visual assessment and fiberoptic cable 45b for infrared thermometry. Between the internal helical fastener 39 and the view window 44, a part of the tubular shaft 46 of the bending portion 16 is sloped to make room for unobstructed forward vision through the view window 44. The sloped portion 43 is elliptically elongated longitudinally along the tubular shaft 46. The fiberoptic cable complex 45 runs longitudinally along the axis to the proximal end 8 as shown in FIG. 1 for direct vision and to the power and control modules 11 and 12, as shown in FIG. 1, for receiving light and for infrared thermometry. Differences in temperature between a target area under therapy and a normal area not receiving therapy are measured by the control module 11 that receives infrared information from both the fiberoptic cables 45b and 57. Conduits 58 and 66 provide water to cleanse the view windows 23 and 44, respectively. The conduits 58 and 66 run longitudinally along the fiberoptic cables 57 and 45 to water ports located at the proximal end 8 as shown in FIG. 1.

Bending cables 68 are attached to the internal helical fastener 39, run longitudinally along the axis of the tubular shaft 46 and are connected to control knobs 9 of the proximal end 8 as shown in FIG. 1 of the Type A flexible tubular device.

FIG. 3A shows a schematic view of the electromagnetic assembly 33, illustrating the coil 61 wound longitudinally along the axis thereof, and magnetic flux controllers 26 and 53 at the front and the back. The outer magnetic flux controller 54 overlying the wound coil 61 is not depicted for illustration of the coil 61. FIG. 3B shows a cross-sectional view of the electromagnetic assembly 33. The magnetic flux controller 54 is semi-circle tubular in shape, encircling the wound coil 61. The coil 61 and 63, which is one continuous single wire, is wound longitudinally along the axis of the inner magnetic flux controller 62. The outer magnetic flux controller encircles the wound coil 61. FIG. 3C shows an example of a schematic profile of the magnetic flux controllers 26 and 53. The space 34 is bordered by the inner wall 32 and inner part of the bottom 64, through which the internal tube 55 passes.

FIGS. 4A and B show a schematic view of an example of distribution of magnetic flux of an electromagnetic field of the electromagnetic assembly 33 of the Type A flexible tubular device. The geometry and location of the magnetic flux controllers 54 and 62 are to amplify electromagnetic field generated from the wound coil 61 and 63 and to concentrate said field on and adjacent to the bottom 64. The bottom 64 is to face or to be in contact with a target area and to be paired electromagnetically with the magnetic materials that are delivered to the target area. The magnetic flux controllers 26, 53 and 54 shield the electromagnetic assembly 33 to reduce unwanted magnetic field to non-target regions and other adjacent electronic devices.

FIG. 5A shows schematic drawings of an example of the bending portion 16 of the tubular shaft 46. The bending portion is fastened to the distal end 15 by the internal helical fastener 39. The tubular shaft 46 comprises a plurality of outer wall layers. Tubular shaft 70-73 is spirally wound along the axis of the tubular shaft 46 in cylindrically helical configurations and is a part of the outer wall complex of said tubular shaft 46. The spirally wound tubular shaft 70-73 is immovably attached distally to the internal helical fastener via round flange 69 and proximally to another round flange of the proximal end 8 as shown in FIG. 1. One helical winding turn is shown as 71 and 72, which is smaller in diameter than 73. FIG. 5B shows a schematic cross-sectional profile view of an individual unit of helix. 75 represents smaller helix and 76 represents larger helix. FIG. 5C shows a schematic view of an example of the larger helix 76 overlapping the smaller helix 75 for a range of length in ways to maintain enfolding overlap between the larger helix 76 and the smaller helix 75 over a range of bending radii of the bending portion 16 of the tubular shaft 46. FIG. 5D shows an example of one of a plurality of methods of spiral winding of strip 79 that is divided in depth in the middle thereof. One longitudinal part of the strip 79 is depressed as in 77 whereas the other longitudinal half is elevated as in 78. The strip 79 is twisted in a circular way 80 to form a spirally wound tubular shaft.

Figure 6:
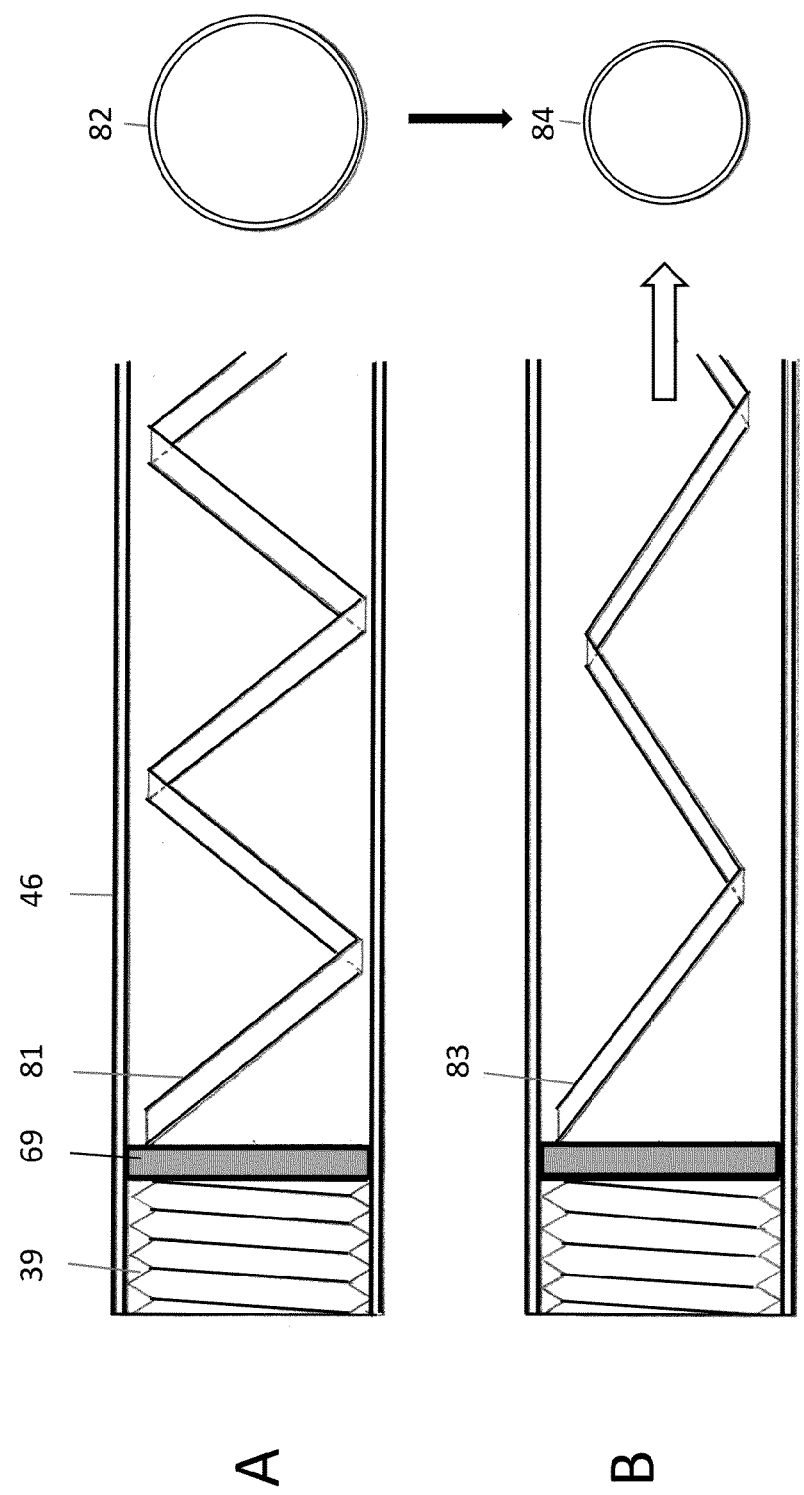
FIG. 6 shows a schematic view of an example of a spiral ribbon that is to encircle and fasten said spirally wound tubular shaft.

FIG. 6 shows a schematic view of an example of one or a plurality of methods of immobilization of the spirally wound tubular shaft 70-73. Spiral ribbon 81 is immovably attached distally to the internal helical fastener 39 via the round flange 69 and runs longitudinally along the axis of the tubular shaft 46 in outer wall space 74 to one control knob of the proximal end 8 as shown in FIG. 1. The ribbon 81 spirally encircles the spirally wound tubular shaft 70-73 in between of the attachment to the flange 69 and to the control knob of the proximal end 8 as shown in FIG. 1. Diameter 82 of the ribbon 81 changes to narrower diameter 84 when the ribbon 81 is pulled up by the control knob toward the proximal end 8 as shown in FIG. 1. The narrower diameter 84 is formed by obtusely angled ribbon 83 from the ribbon 81. The ribbon 83 with the narrower diameter 84 releasably fastens and immobilizes the spirally wound tubular shaft 70-73. Once the control knob releases the ribbon 83 back toward the distal end 15, the ribbon 83 becomes the ribbon 81 with the wider diameter 82, thereby releasing the spirally wound tubular shaft 70-73.

Figure 7:
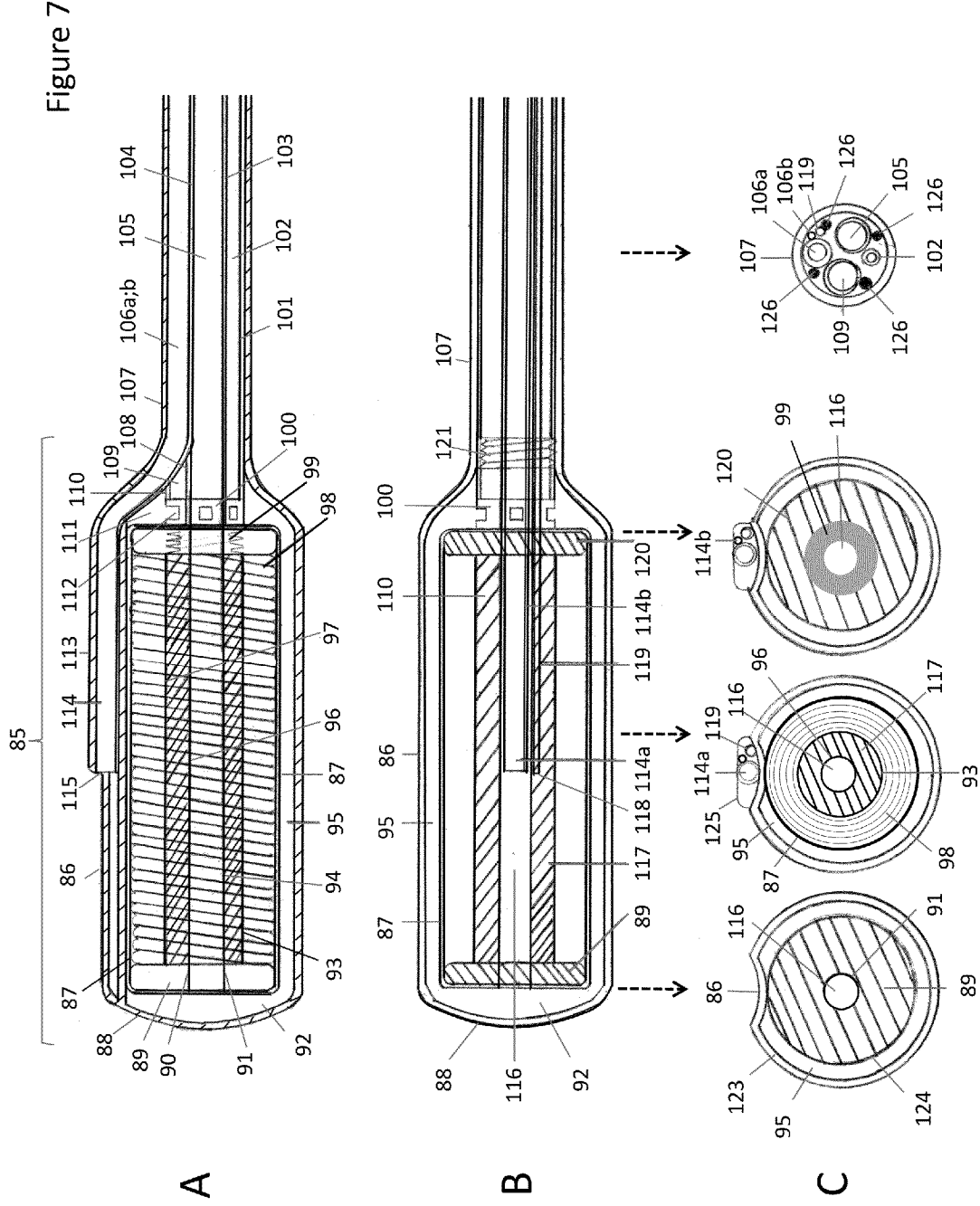
FIG. 7 shows a schematic view of an example of a distal end of Type B flexible tubular device.

FIG. 7 shows a schematic drawings of an example of distal end and a part of bending portion of Type B flexible tubular device. FIG. 7A shows a side view of said device; 7B a top-down view; 7C cross-sectional views. Electromagnetic assembly 87 is surrounded by enclosure 86 of circular cylinder with its round bottom 88 located at the front of the distal end 85. The enclosure 86 is proximally bordered by internal helical fastener 121. The bending portion starts at the internal helical fastener 121 and runs for a range of length of tubular shaft 107 longitudinally along the axis toward the proximal end 8 as shown in FIG. 1.

The enclosure 86 surrounds the electromagnetic assembly 87, water distribution hub 100, areas of water circulation space 92, 95 and 111, and part of conduits 102, 105 and 109. The water space 92 is bordered by inner wall of the round bottom 88. The water space 95 is bordered by inner wall 123 of the enclosure 86 and outer wall 124 of electrically conductive coil 98. The water space 111 is bordered by proximal part of the enclosure 86. The enclosure 86 is made of one or a plurality of heat resistant polymers that have a range of thermal tolerance beyond maximum temperature produced by the electromagnetic assembly 87.

The electromagnetic assembly 87 comprises the electrically conductive coil 98 that is continuously and radially wound around hollow tubular magnetic flux controller 117 at the right angle to the axis of the electromagnetic assembly 87 and magnetic flux controllers 89, 117 and 120. The electrically conductive coil is bordered with outer walls 93 and 97 of the magnetic flux controller 117. The electrically conductive coil 98 is connected to electrically conductive wire 102 that runs proximally inside the tubular shaft 107 to the power and control modules 11 and 12 as shown in FIG. 1 and receives electric current therefrom. The electrically conductive coil 98 is insulated by heat resistant polymers. The electrically conductive wire 102 is bordered by wall 101 and 103, which are insulated by heat resistant polymers. The magnetic flux controller 117 has hollow tubular center 116 located longitudinally along the axis thereof. The hollow tubular center is bordered by inner walls 94 and 96 of the magnetic flux controller 117. The hollow tubular center 116 is communicated distally to the space 92 through opening 90-91 located in the center of the magnetic flux controller 89 and proximally to the water distribution hub 100 via gap seal 99 located in the center of the magnetic flux controller 120.

Magnetic flux controllers 89, 117 and 120 are to amplify and concentrate magnetic field on and around the electromagnetic assembly 87 radially distributed along the longitudinal axis thereof. North and south poles of magnetic field are formed on both magnetic flux controllers 89 and 120.

Cooling of the electromagnetic assembly 87 is achieved by circulation of water in the distal end 85. Water inflow conduit 109 runs distally from the power and control modules 11 and 12 as shown in FIG. 1 inside the tubular shaft 107, goes through the water distribution hub 100 and terminates as a central opening in the middle of the gap seal 99. The water inflow conduit 109 inside the enclosure 86 is bordered by wall 108 and 110. The central opening of the gap seal 99 communicates directly with the hollow tubular center 116. The hollow tubular space 116 opens to the water space 92. The areas of water space 92, 95 and 111 are communicated with each other as single continuous space. The water distribution hub 100 on its side wall has a plurality of holes 112 that communicate with the space 111. The water distribution hub 100 is connected to water outflow conduit 105 that runs inside the tubular shaft 107 longitudinally along the axis to the power and control modules 11 and 12. The water outflow conduit 105 is bordered by wall 103 and 104. The power and control modules 11 and 12 provide the water inflow conduit 109 with pressure water and suction off returning water from the water outflow conduit 105. Suctioning of water occurs at the water distribution hub 100 whereby water is suctioned in by negative pressure through the holes 112. The power and control modules 11 and 12 measure temperature of both inflow and outflow of water and regulate volume, speed and temperature of circulating water to cool down the electromagnetic assembly 87 to preset operating temperature. The power and control modules 11 and 12 have a heat exchange unit for circulating water.

Forward looking fiberoptic cable complex 114 is located longitudinally on the exterior of the distal end 85, in a groove on the top of the enclosure 86. Said cable complex comprises fiberoptic cable for vision 114a ans fiberoptic cable for infrared thermometry 114b that runs in parallel with the 114a. View window 115 is located in front of the fiberoptic cable complex 114, preferably in the middle of the groove of the enclosure 86. The fiberoptic cable complex 114 is bordered by outer wall 113 that merges with the outer wall of the tubular shaft 107. The fiberoptic cable complex 114 outside the distal end becomes inner cable complex 106 inside the tubular shaft 107 proximally above the internal helical fastener 121. The inner cable complex 106 comprises fiberoptic cable for vision 106a and fiberoptic cable 106b for infrared thermometry. The fiberoptic cable complex 106 runs inside longitudinally along the axis of the tubular shaft 107 to the proximal end 8 as shown in FIG. 1 for direct vision and to the power and control modules 11 and 12, as shown in FIG. 1, for receiving light and for infrared thermometry. Water washer conduit 119 is located adjacent to and runs together with the fiberoptic cable complexes 114 and 106 toward the proximal end 8 as shown in FIG. 1. The water washer conduit 119 receives water through a port at the proximal end 8 as shown in FIG. 1 to cleanse the view window 115. Both the fiberoptic cable complex 114 and water washer conduit 119 are enclosed by protective cover 125 for the portion located on the exterior of the distal end 85. The protective cover 125 merges proximally with the outer wall of the tubular shaft 107.

Figure 8:
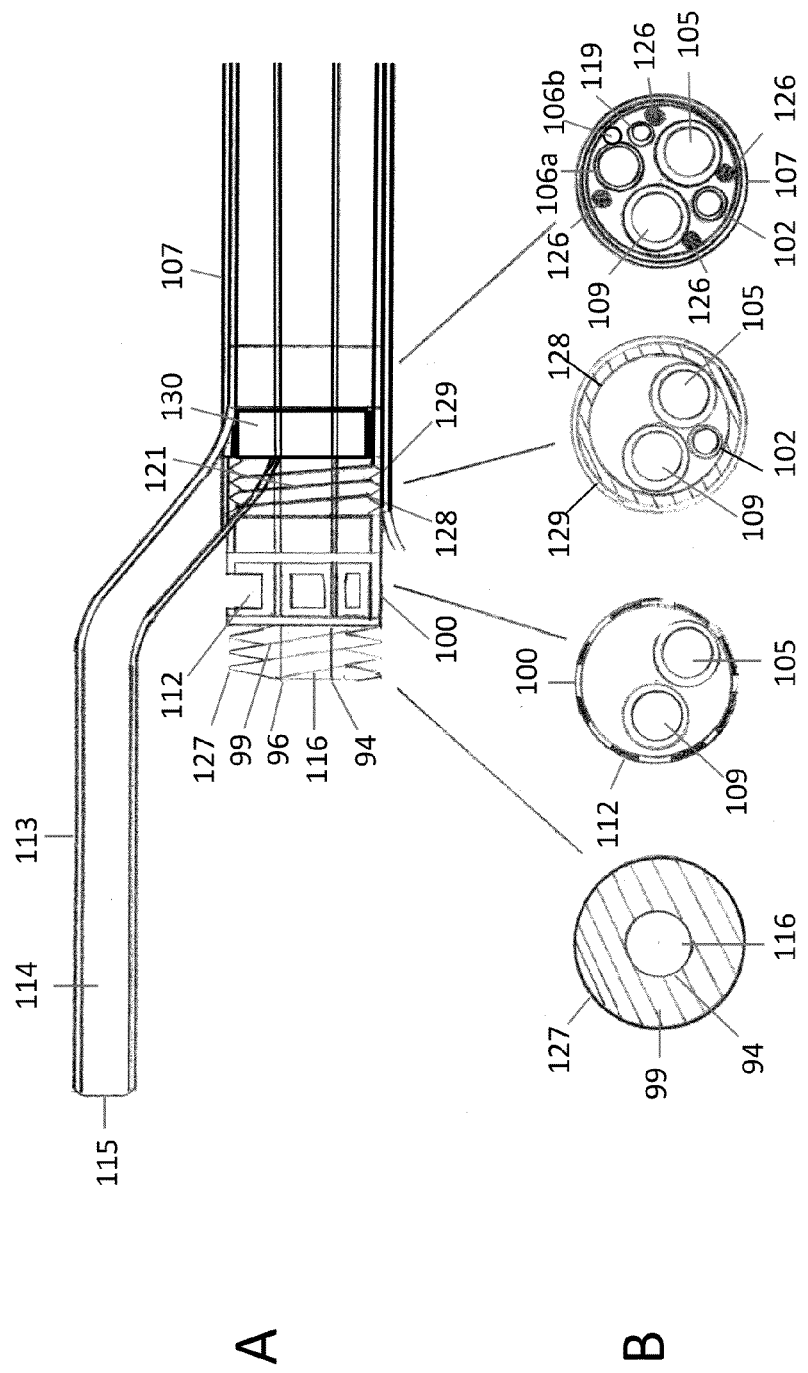
FIG. 8 shows a schematic view of an example of a flexible tubular shaft of Type B and its fiberoptic cable of said flexible tubular device of the FIG. 7.

Referring to FIG. 7, FIG. 8 shows detailed views of assemblage of the fiberoptic cable complex 114, the gap seal 99, the water distribution hub 100, the internal helical fastener 121, flange 130 of the internal helical fastener 121, a plurality of conduits and bending cables 126. FIG. 8A shows a side view and FIG. 8B shows cross-sectional views. The gap seal 99 screws into the central opening of the magnetic flux controller 120 that corresponds to helical edges 127 for tight fitting. The gap seal is doughnut shaped, with its hollow center 116 bordered by inner wall 94 and 96, The hollow center 116 is a part of the hollow tubular center 116 of the magnetic flux controller 117. The water inflow conduit 109 passes through the water distribution hub 100 to get connected to the hollow center 116 of the gap seal 99. The water outflow conduit 105 opens to and terminates at the water distribution hub. The water distribution hub has a plurality of the holes 112 through which water is suctioned off into the water outflow conduit 105.

The internal helical fastener 121 seals off proximally the distal end 85 and serves as attachment for bending cables 126. Thickness of the internal helical fastener is defined by peak 129 and valley 128. The bending portion of said device starts at the internal helical fastener 121 and runs for a range of length of the tubular shaft 107. The bending cables 126 are attached to the flange 130 of the internal helical fastener 121, run longitudinally along the axis of the tubular shaft 107 and are connected to control knobs 9 of the proximal end 8 as shown in FIG. 1 of the Type B flexible tubular device.

Figure 5:
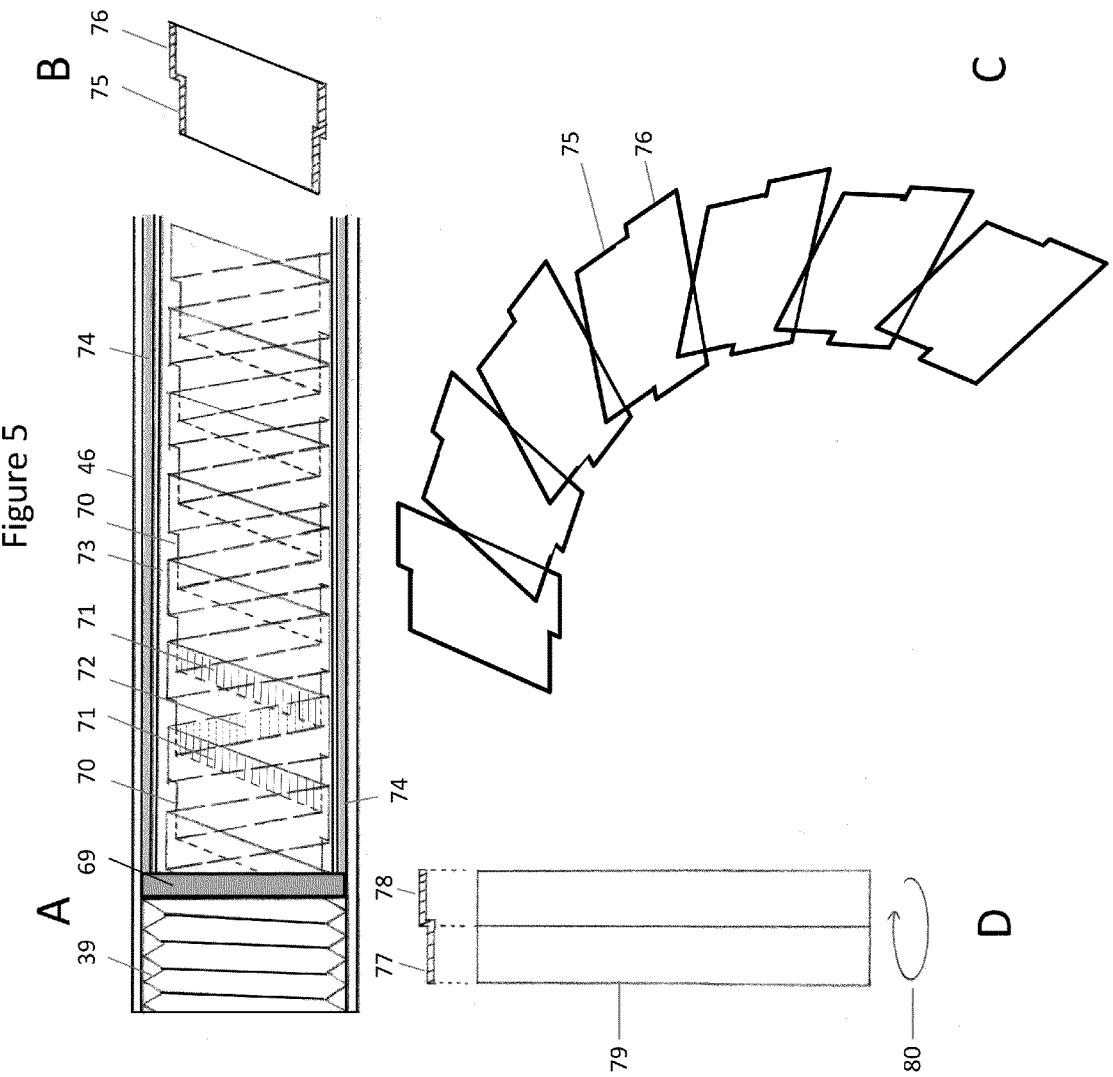
FIG. 5 shows a schematic view of an example of a spirally wound tubular shaft of a bending portion of a flexible fiberoptic tubular device.

Referring to FIGS. 5 and 6, the Type B flexible tubular device comprises one or a plurality of spirally wound tubular shafts and spiral ribbons of similar mechanical configurations to the spirally wound tubular shaft 70-73 and the spiral ribbon 81 of the Type A device, which control and stabilize said bending portion of said tubular shaft 107 of the Type B device.

Figure 9:
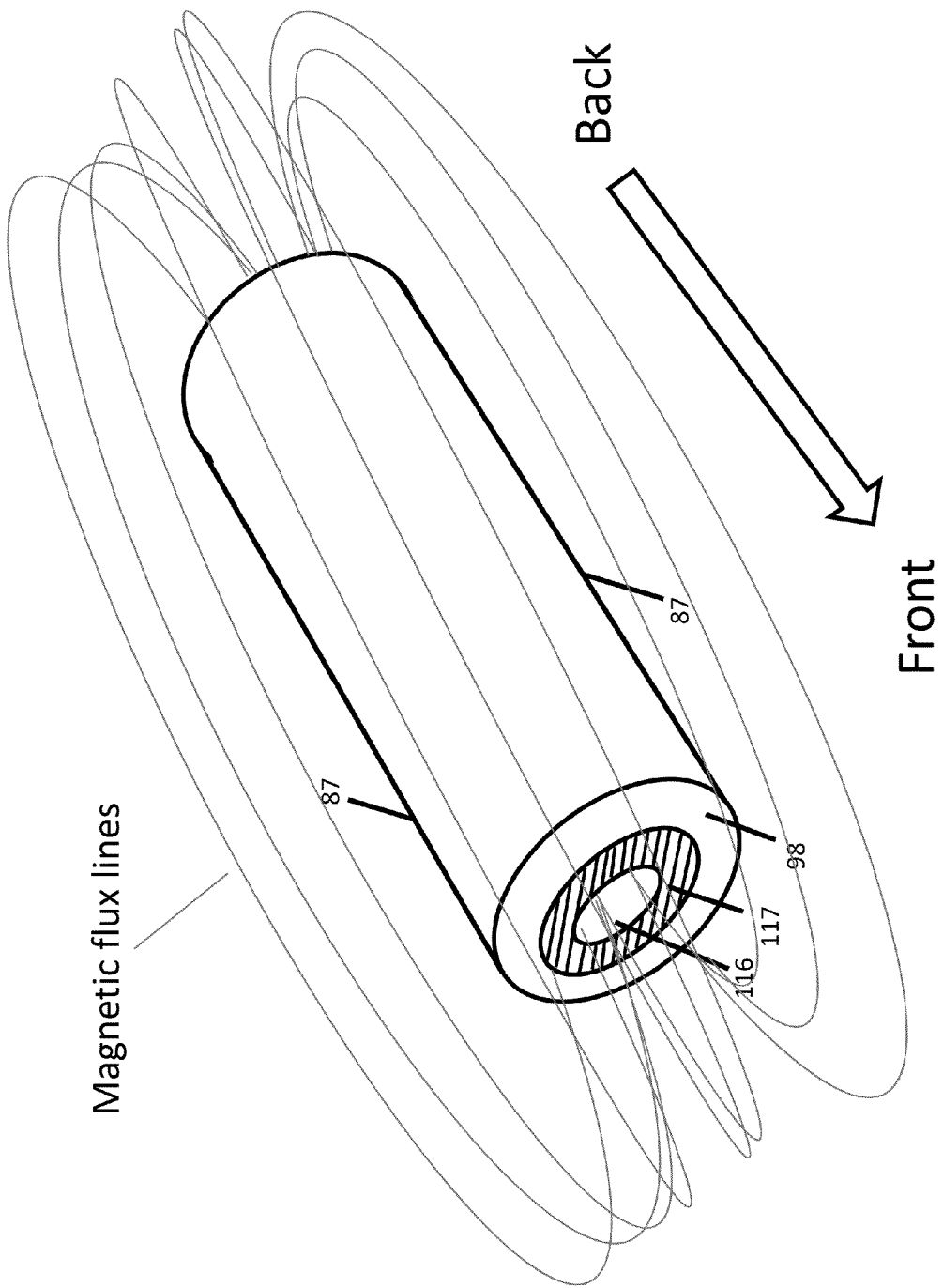
FIG. 9 shows a schematic view of an example of an electromagnetic assembly of Type B with both of its ends exposed and of distribution of magnetic flux of electromagnetic field.

FIG. 9 depicts a schematic view of an example of distribution of electromagnetic field in and around the electromagnetic assembly without magnetic flux controllers 89 and 120. The hollow tubular magnetic flux controller 117 is to amplify electromagnetic field generated by the wound coil 98. The most intense magnetic field is located longitudinally along the axis inside the hollow tubular center 116 and on immediately adjacent areas to the electromagnetic assembly 87. Said assembly 87 emits electromagnetic field radially along the longitudinal axis thereof, in elliptical circles. The elliptical circles start from one end of said assembly 87 and return to the other end of said assembly 87. The distribution of the electromagnetic field is most suitable for magnetic materials deployed in tubular structure that surrounds said assembly 87.

Figure 10:
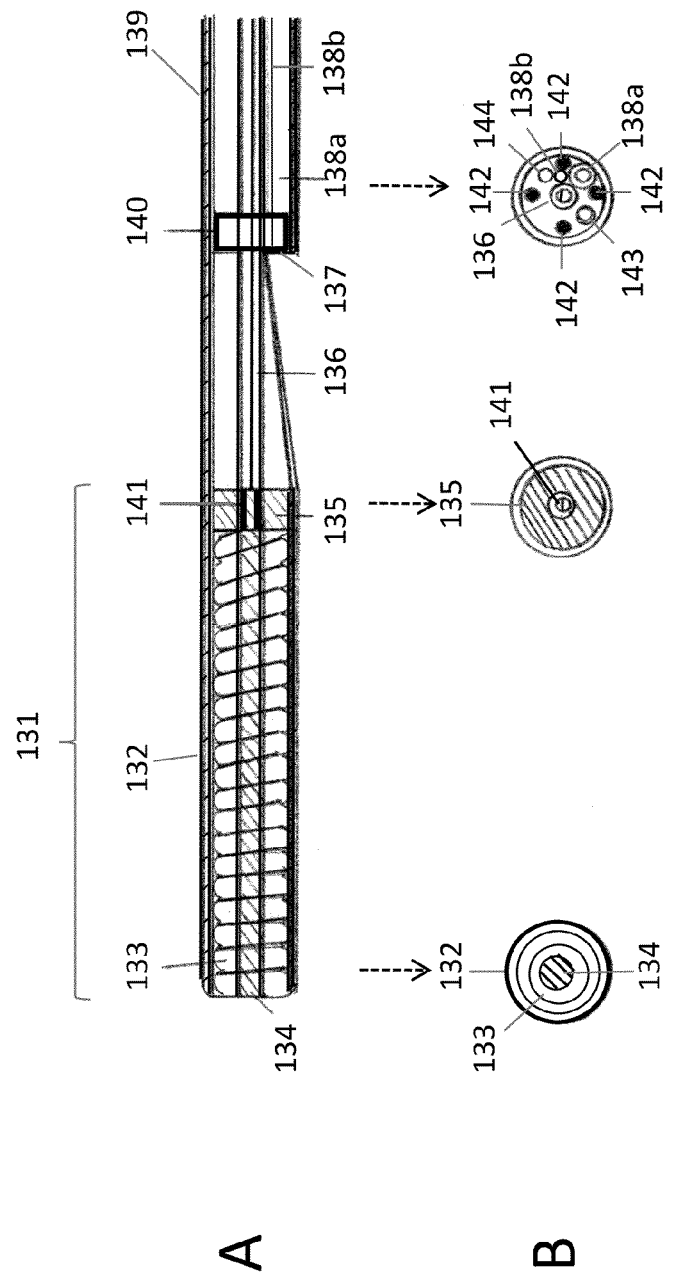
FIG. 10 shows a schematic view of an example of Type C flexible tubular device.

FIG. 10 illustrates a schematic view of an example of distal end and part of bending portion of Type C flexible tubular device. Water cooling system is not provided for the Type C device. FIG. 10A shows a side view and FIG. 10B shows cross-sectional views. Distal end 131 comprises tubular outer wall 132, wound coil 133, round longitudinal rod shaped magnetic flux controller 134, doughnut-shaped magnetic flux controller 135 and temperature detectors 141. The electrically conductive coil 133 is continuously and radially wound around the round longitudinal rod shaped magnetic flux controller 134 at the right angle to the axis, goes through the open center of the magnetic flux controller 135 and is connected to electrically conductive wire 136 that runs longitudinally along the axis of tubular shaft 139 to the power and control modules 11 and 12 as shown in FIG. 1 and receives electric current therefrom. The temperature detectors 141 are resistant temperature detectors attached to the electrically conductive coil 133 in the magnetic flux controller 135. Said detectors 141 are connected to electrically conductive wire 144 that runs longitudinally along the axis of the tubular shaft 139 to the power and control modules 11 and 12. Said power and control modules 11 and 12 monitor temperature of the distal end 131 and regulate electricity to said end 131.

Forward looking fiberoptic cable complex 138 is located in the bending portion of the tubular shaft 139, exposed to the side of the exterior thereof, with its view window 137 faced forward and runs longitudinally along the axis to the proximal end 8 as shown in FIG. 1 for direct vision and to the power and control modules 11 and 12, as shown in FIG. 1, for receiving light and for infrared thermometry. The fiberoptic cable complex comprises fiberoptic cable for vision 138a and fiberoptic cable for infrared thermometry 138b that runs together with the 138a. Water washer 143 runs in parallel with the fiberoptic cable complex 138 inside the tubular shaft 139, to a water port of the proximal end 8 as shown in FIG. 1. The water washer opens next to and cleanses the view window 137.

Between the magnetic flux controller 135 and the view window 137, a part of the tubular shaft 139 is sloped to make room for unobstructed forward vision through the view window 137. The sloped portion is elliptically elongated longitudinally along the tubular shaft 139.

Bending cables 142 are internally attached to bending cable attachment site 140. The bending cables 142 run longitudinally along the axis of the tubular shaft 139 to control knobs 9 of the proximal end 8 as shown in FIG. 1.

Continuing to refer to FIGS. 5 and 6, the Type C flexible tubular device comprises one or a plurality of spirally wound tubular shafts and spiral ribbons of similar mechanical configurations to the spirally wound tubular shaft 70-73 and the spiral ribbon 81 of the Type A device, which control and stabilize said bending portion of said tubular shaft 139 of the Type C device.

Figure 11:
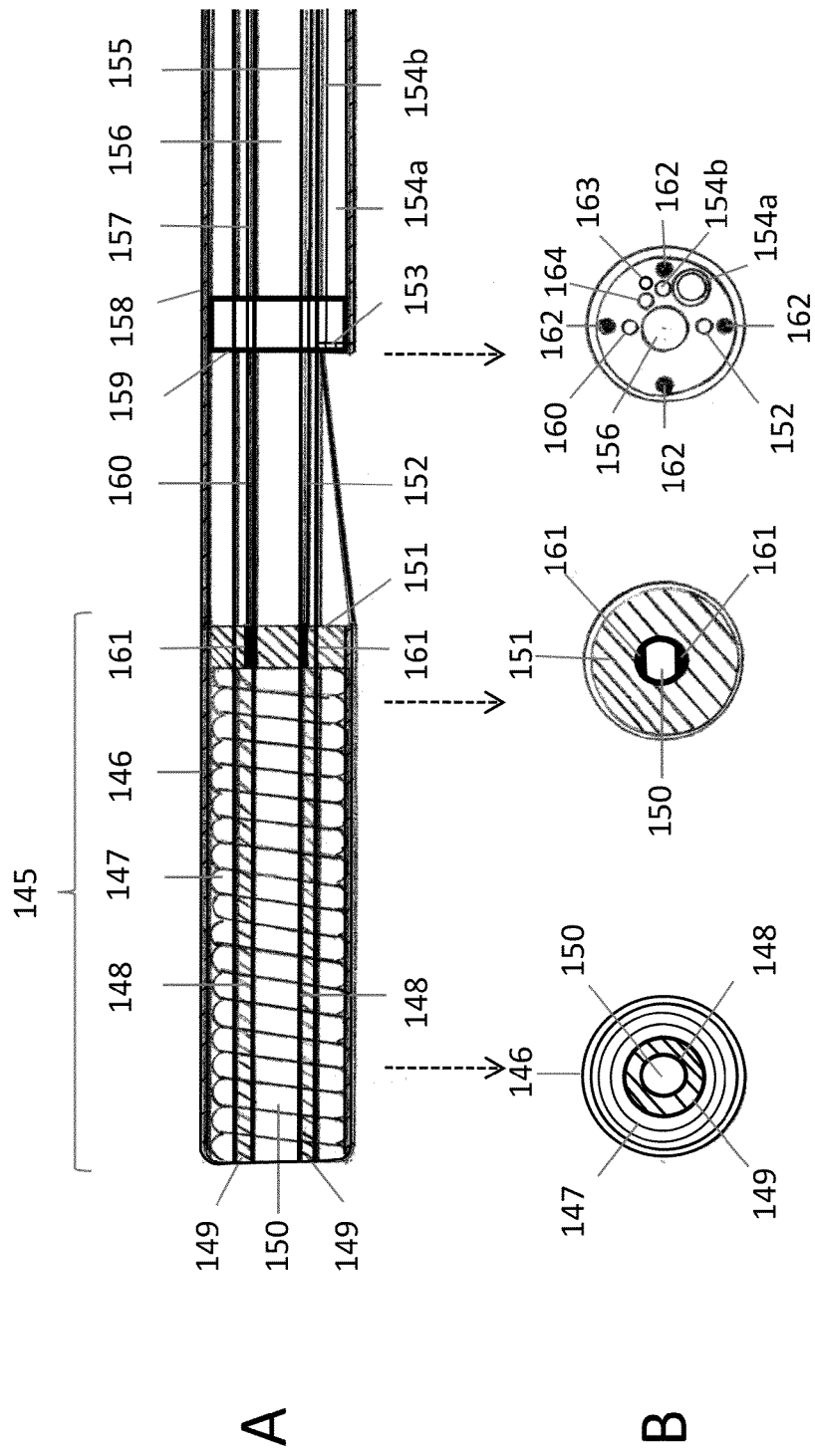
FIG. 11 shows a schematic view of an example of Type D flexible tubular device.

FIG. 11 illustrates a schematic view of an example of distal end and part of bending portion of Type D flexible tubular device. Closed water cooling system is not provided for the Type D device. FIG. 11A shows a side view and FIG. 11B shows cross-sectional views. Distal end 145 comprises tubular outer wall 146, wound coil 147, hollow-tube-shaped magnetic flux controller 149, doughnut-shaped magnetic flux controller 151 and temperature detectors 161. The electrically conductive coil 147 is continuously and radially wound around the hollow-tube-shaped magnetic flux controller 149 at the right angle to the axis, goes through open hole 150 of the magnetic flux controller 151 and is connected to electrically conductive wires 152 and 160 that run longitudinally along the axis of tubular shaft 158 to the power and control modules 11 and 12 as shown in FIG. 1 and receives electric current therefrom. The temperature detectors 161 are resistant temperature detectors attached to the electrically conductive coil 147 in the open hole 150 of the magnetic flux controller 151. Said detectors 161 are connected to electrically conductive wire 164 that runs longitudinally along the axis of the tubular shaft 158 to the power and control modules 11 and 12. Said power and control modules 11 and 12 monitor temperature of the distal end 145 and regulate electricity to said end 145.

Forward looking fiberoptic cable complex 154 is located in the bending portion of the tubular shaft 158, exposed to the side of the exterior thereof, with its view window 153 faced forward and runs longitudinally along the axis to the proximal end 8 as shown in FIG. 1 for direct vision and to the power and control modules 11 and 12, as shown in FIG. 1, for receiving light and for infrared thermometry. The cable complex 154 comprises fiberoptic cable for vision 154a and fiberoptic cable for infrared thermometry 154b that runs together with the 154a. Water washer 163 runs in parallel with the fiberoptic cable complex 154 inside the tubular shaft 158, to a water port of the proximal end 8 as shown in FIG. 1. The water washer opens next to and cleanses the view window 153.

Between the magnetic flux controller 151 and the view window 153, a part of the tubular shaft 158 is sloped to make room for unobstructed forward vision through the view window 153. The sloped portion is elliptically elongated longitudinally along the tubular shaft 158.

Bending cables 162 are internally attached to bending cable attachment site 159. The bending cables 162 run longitudinally along the axis of the tubular shaft 158 to control knobs 9 of the proximal end 8 as shown in FIG. 1.

Continuing to refer to FIGS. 5 and 6, the Type D flexible tubular device comprises one or a plurality of spirally wound tubular shafts and spiral ribbons of similar mechanical configurations to the spirally wound tubular shaft 70-73 and the spiral ribbon 81 of the Type A device, which control and stabilize said bending portion of said tubular shaft 158 of the Type D device.

There is provided conduit 150 in the middle of the distal end 145. The conduit 150 is bordered by inner wall 148 of the magnetic flux controller 149 and runs longitudinally along the axis inside the magnetic flux controller 149 and is connected to conduit 156 located in the middle of the tubular shaft 158. The conduit 156 is bordered by wall 155 and 157, runs longitudinally along the axis of the tubular shaft 158 and is connected to a port of the proximal end 8 as shown in FIG. 1 of said device. The conduits 156 and 150 are to provide water, air or other substances to a target area, or to deliver catheter, guidewire or thermal coil to the target area.

Figure 12:
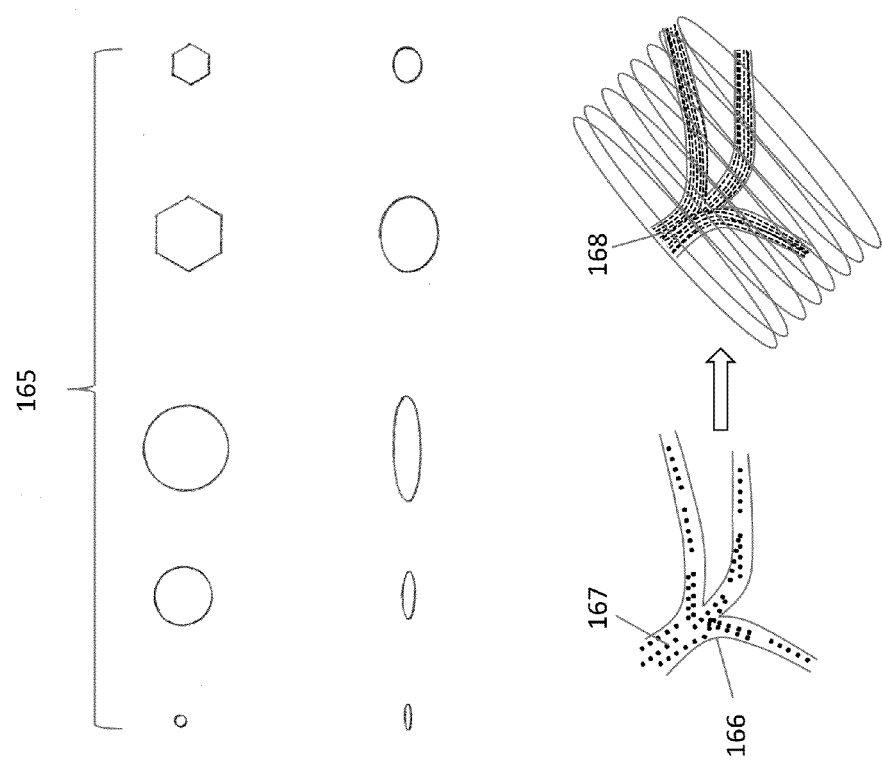
FIG. 12 shows a schematic view of examples of magnetic particles and transphasic fluid in blood vessels.

FIG. 12 illustrates a schematic view of examples of magnetic materials that are to be dissolved in transphasic fluid and to be deployed to biologic tissue and to be paired with flexible tubular device. Magnetic particles 165 are spherical, elliptically spherical, elliptical-rod, or multi-faceted in shape and range from 1 nanometer to few hundreds micrometers in size. The magnetic particles comprise one or a plurality of metallic materials and are ferromagnetic, paramagnetic or superparamagnetic and radiographically visible. The magnetic particles 167 suspended in transphasic fluid are to be introduced by vascular catheterization to target blood vessels 166 connected to the target area and to be removed by magnetic blood centrifuge machine following completion of therapy. Said magnetic particles 167 become aligned along magnetic flux lines once static electromagnetic field is applied, and form magnetically reversibly linked random lattice structure 168 under said direct electromagnetic field. Said lattice structure increases viscosity of said transphasic fluid, thereby changing said fluid in liquid phase to said fluid in gel-like or semi-solid phase. Said transphasic fluid comprises magnetic particles of different sizes and shapes combined together at varying ratios to optimize one or a plurality of shear strengths and particle sedimentations of magnetorheological property of said fluid.

Figure 13:
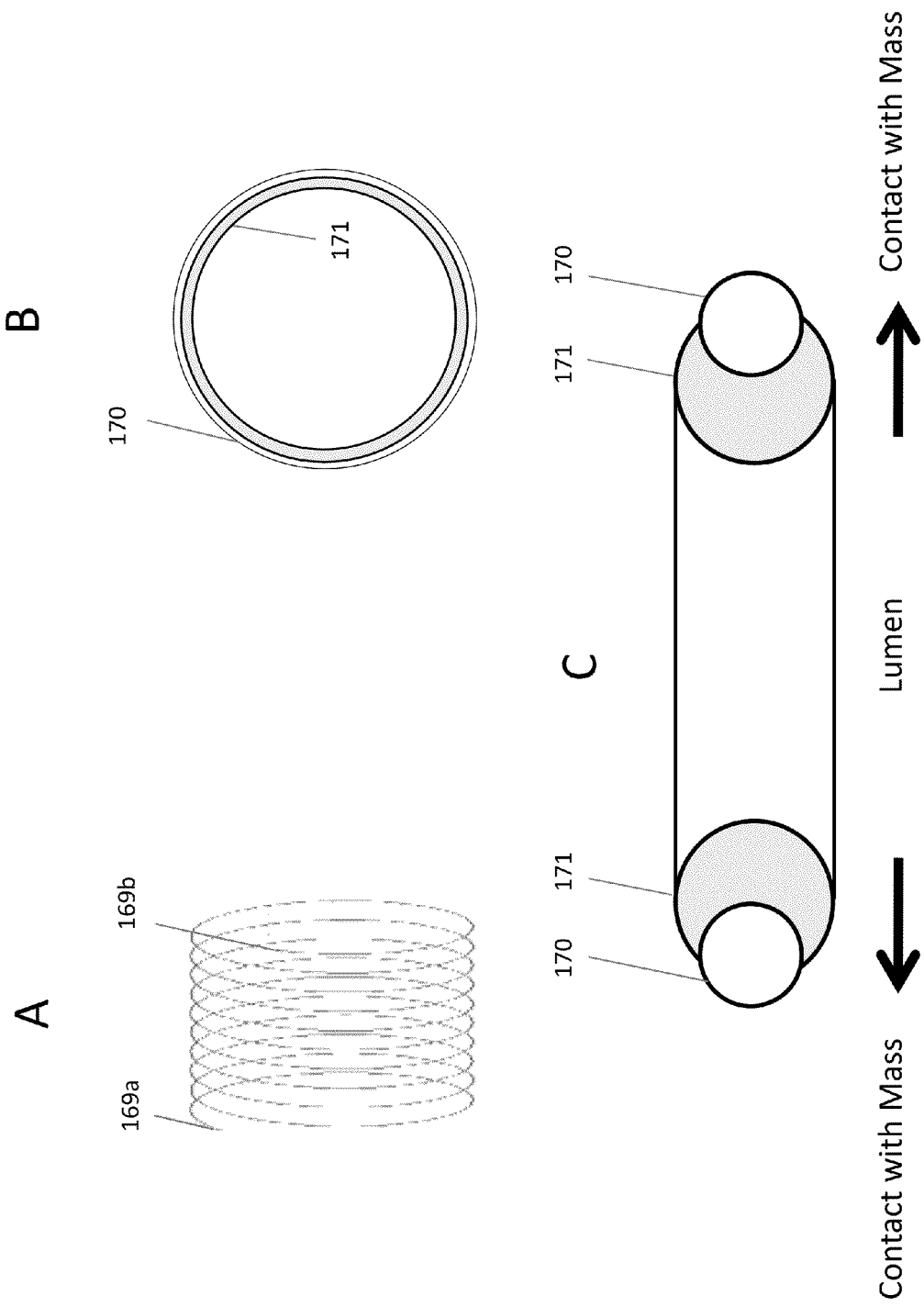
FIG. 13 shows a schematic view of one example of thermal coil.

FIG. 13 displays a schematic view of one example of thermal coil. FIG. 13A shows a side view of thermal coil; 13B shows an axially cross-sectional view of thermal coil; 13C shows a cross-sectional cut surface view of thermal coil. There are a plurality of shapes, sizes and configurations of thermal coil. In one embodiment, thermal coil is shaped as cylindrically helical longitudinally along the axis and proximal point 169a advances into a lumen or a cavity and distal point 169b may be attached to a means for delivery of said thermal coil.

To a large extent, heated thermal coil transfers heat energy to contacted tissues of a target area via conduction and to an open area of a lumen or a cavity via convection. Therefore, it is important to increase efficiency of conduction of heat energy to said tissues in contact with said thermal coil, and to decrease convective heat to said open area to avoid unwanted heating of said lumen or said cavity and consequent loss of heat energy. Efficiency of heat transfer from said thermal coil to said tissues improves by increase in contact pressure of said thermal coil to said tissues and by increase in ratio of contact mass of said thermal coil to contact mass of said tissues. In one embodiment, one or a plurality of thermal coils are constructed for a range of outward radial pressure and for a range of thickness and density of one or a plurality of thermal materials to optimize delivery of heat energy to target tissues. The cross-sectional view 13B shows thermal material 170 of thermal coil located outside of helical cylinder of said thermal coil and thermal barrier 171 made of one or a plurality of heat resistant polymers, located inside of said cylinder of said thermal coil. The cross sectional cut surface of thermal coil 13C shows the thermal material 170 being encased to a range of its circumference by the thermal barrier 171. The thermal material 170 has one or a plurality of configurations. One example of configuration is rod-shaped round coil. Thermal coil comprises one or a plurality of thermal materials. Thermal material comprises one or a plurality of metals or alloys, which may be shape memory alloy.

Figure 14:
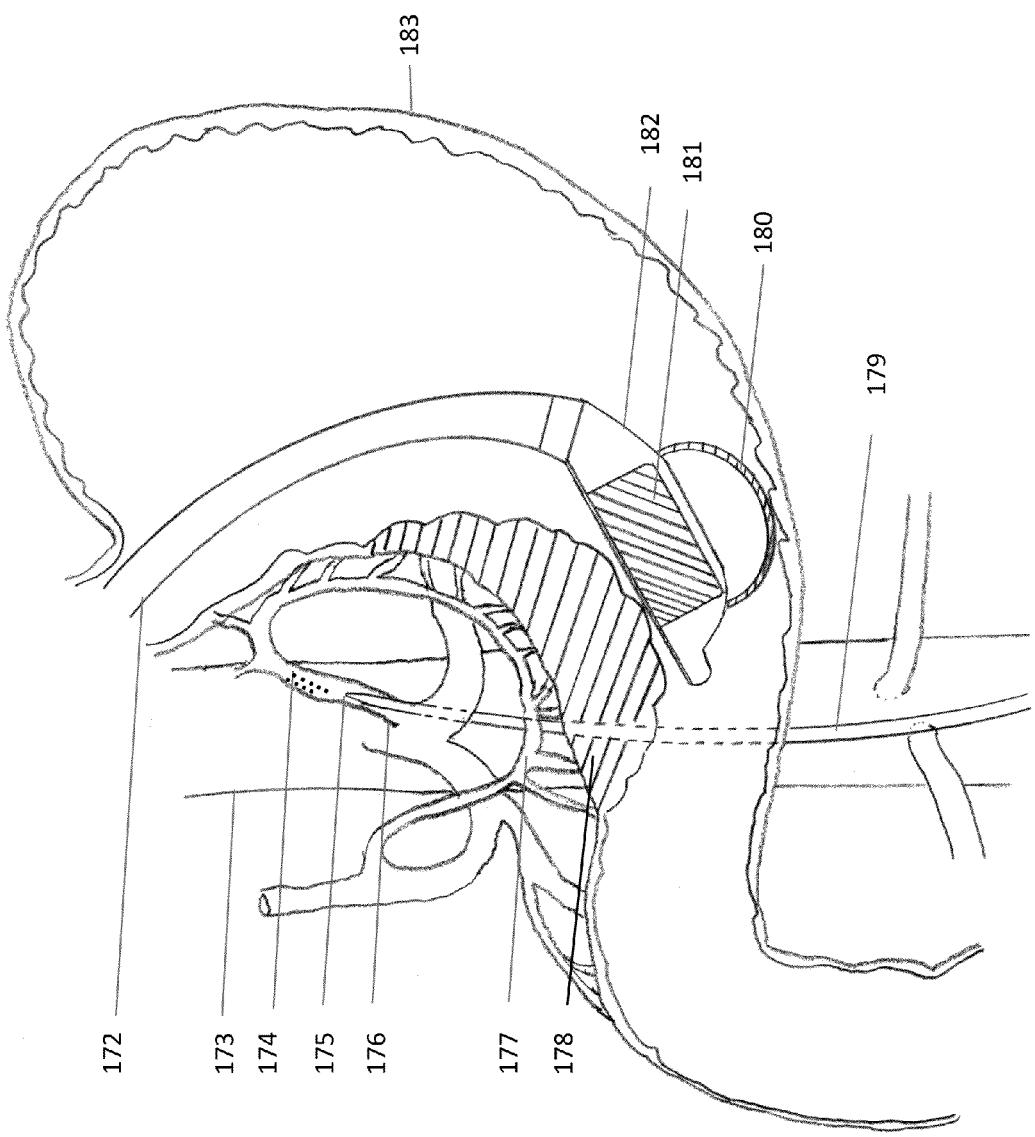
FIG. 14 illustrates a schematic explanatory view of an example of a deployment of a flexible tubular device in a stomach close to a cancer in the wall of the stomach.

FIG. 14 illustrates a schematic explanatory view of an example of thermal therapy of a stomach mass 178 by Type A flexible tubular device 172 and magnetic materials 174 introduced by an arterial catheter 179 inserted into a branch 176 of celiac axis of descending aorta 173 of a human body. First, the Type A flexible tubular device 172 is introduced to stomach 183 by fiberoptic visual navigation. Distal end 182 of said device 172 is placed on the stomach mass 178 and position of said distal end 182 is stabilized by inflation of air balloon 180 that expands to fill up hollow space of the stomach 183. Following firm positioning of said distal end 182, the arterial catheter 179 is introduced into the descending aorta 173 and catheter tip 175 of said catheter 179 is positioned into the branch 176 of the celiac axis. Said arterial branch 176 provides the stomach mass 178 with blood via local arterial branches 177. Following confirmation of location of said catheter tip 175 in the branch 176 by x-ray fluoroscopy, a test dose of the magnetic materials 174 in transphasic fluid is introduced to said branch 176 through said catheter tip 175 while electromagnetic assembly 181 of said distal end 182 produces one or a plurality of static electromagnetic fields. Under said static magnetic field attracting said magnetic materials 174 close to said assembly 181, said magnetic materials 174 move toward said stomach mass 178 through said arterial branches 177. Localization of the test dose of said magnetic materials 174 is confirmed by x ray. Once confirmed for the localization of said materials 174, a treatment dose of said material 174 in transphasic fluid is introduced by the same technique as aforementioned under the static electromagnetic field. Following confirmation of concentration of the treatment dose of said materials 174 around said stomach mass 178 by x ray, said assembly 181 produces one or a plurality of alternating electromagnetic fields that make said materials 174 generate heat.

Figure 15:
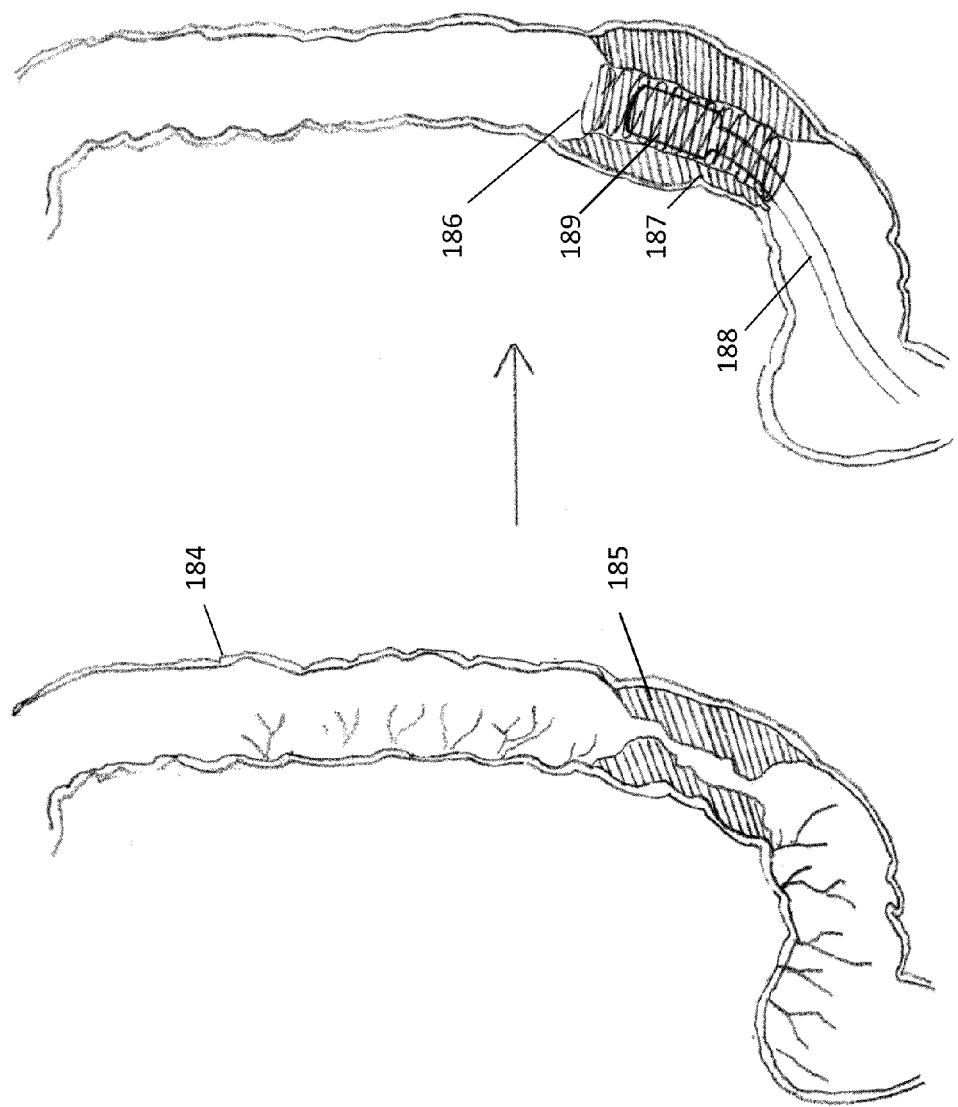
FIG. 15 illustrates a schematic explanatory view of an example of a deployment of a flexible tubular device into an open thermal coil inside of an intestine.

FIG. 15 depicts a schematic explanatory view of an example of thermal therapy of an intestinal mass 185 that nearly obstructs a segment of intestine 184. First, an expandable thermal coil 186 is deployed by one or a plurality of methods inside lumen of said intestinal mass 185. Said expanded thermal coil 186 exerts outward pressure to the lumen of said mass 185 that becomes a mass 187, having tight contact between the coil 186 and the mass 187 to reduce thermal resistance at the border between 186 and 187. Following confirmation of tight contact of said coil 186 with said mass 187 and of location of said thermal coil 186 abutting on inner wall of said mass 187, a flexible tubular device 188 is introduced by fiberoptic visual navigation. Distal end 189 of said flexible tubular device is inserted into the center of said thermal coil 186. One or a plurality of alternating electromagnetic fields is produced from said distal end 189 that comprises an electromagnetic assembly inside and receives one or a plurality of alternating electric currents. Said alternating electromagnetic field makes said thermal coil 186 generate heat that is delivered to said mass 187.

Figure 16:
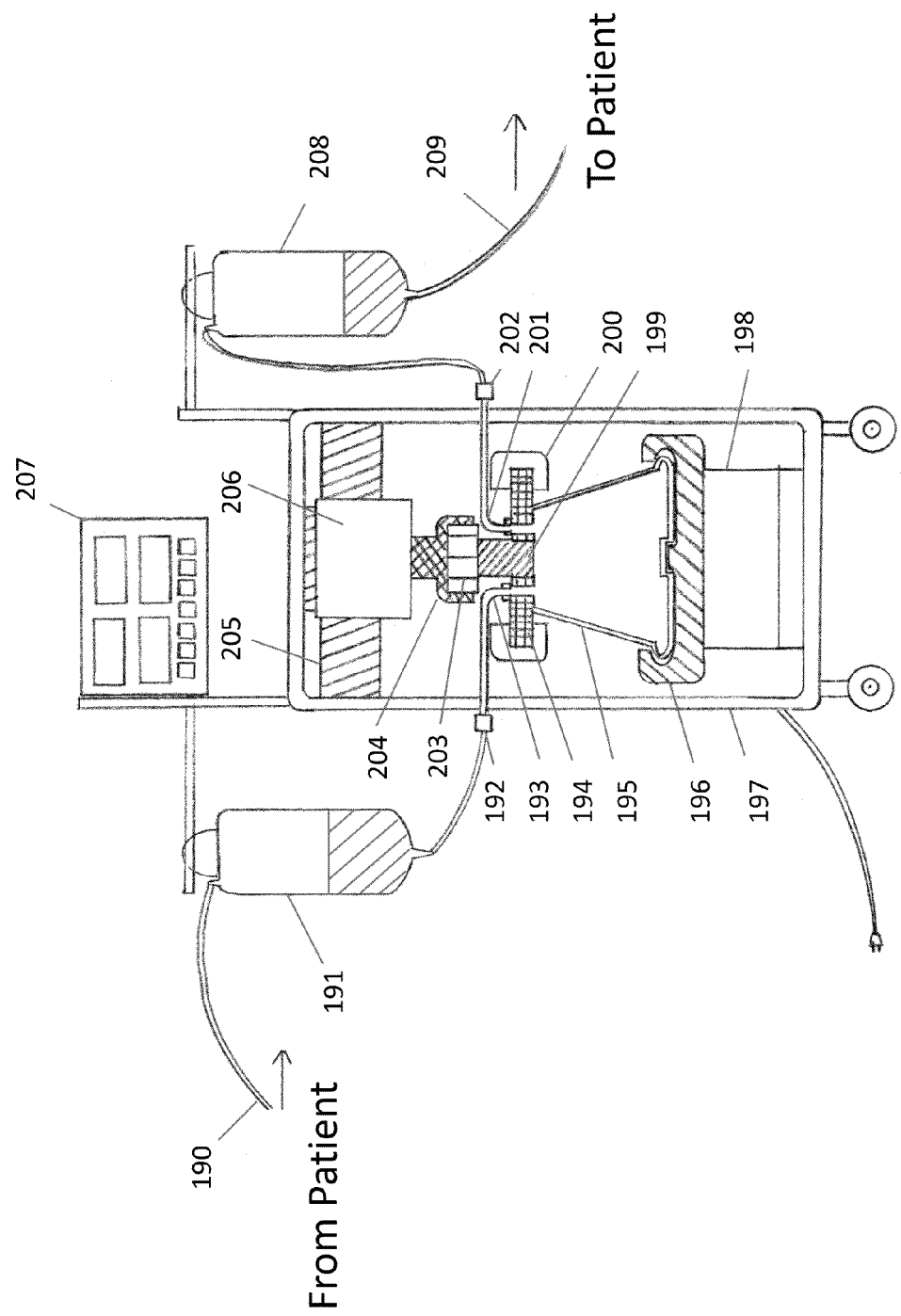
FIG. 16 shows a schematic explanatory view of an example of a magnetic centrifuge machine.

FIG. 16 illustrates a schematic view of an example of magnetic blood centrifuge. One blood vessel of patient is connected to conduit 190 that delivers blood from patient to collection bag 191. The collection bag 191 is connected to intake port 192. The intake port 192 is connected to inflow tube 193 that leads to rotatable centrifuge chamber 195. Said centrifuge chamber 195 is releasably surrounded by one or a plurality of static magnets 196 at the bottom and on the side wall for a range of length thereof. Said static magnets are stabilized distally by support 198. Said centrifuge chamber 195 is connected to rotating assembly 194 located on the top thereof. The rotating assembly 194 is surrounded by support 200 that securely allows rotation of said assembly 194 and said chamber 195. The rotating assembly 194 has immovable central shaft 199 that is connected to head 203 of said shaft.

The shaft head 203 is releasably coupled with rotor coupler 204. The rotor coupler 204 is connected to rotor 206 that is stabilized by support 205 surrounding the side wall of said rotor 206. The rotor 206 provides said centrifuge chamber 195 with rotation. Centrifuge assembly and rotor assembly are housed in case 197. Control module 207 provides electricity, monitors centrifugation, magnetic field strength of said magnets and efficiency of removal of magnetic materials from blood, and regulates the rotor 206 and inflow and outflow of blood. Blood that has been centrifuged is sent to collection bag 208 via outflow tube 201 and outflow port 202. The collection bag 208 delivers said blood back to patient through conduit 209 to complete the cycle.

Figure 17:
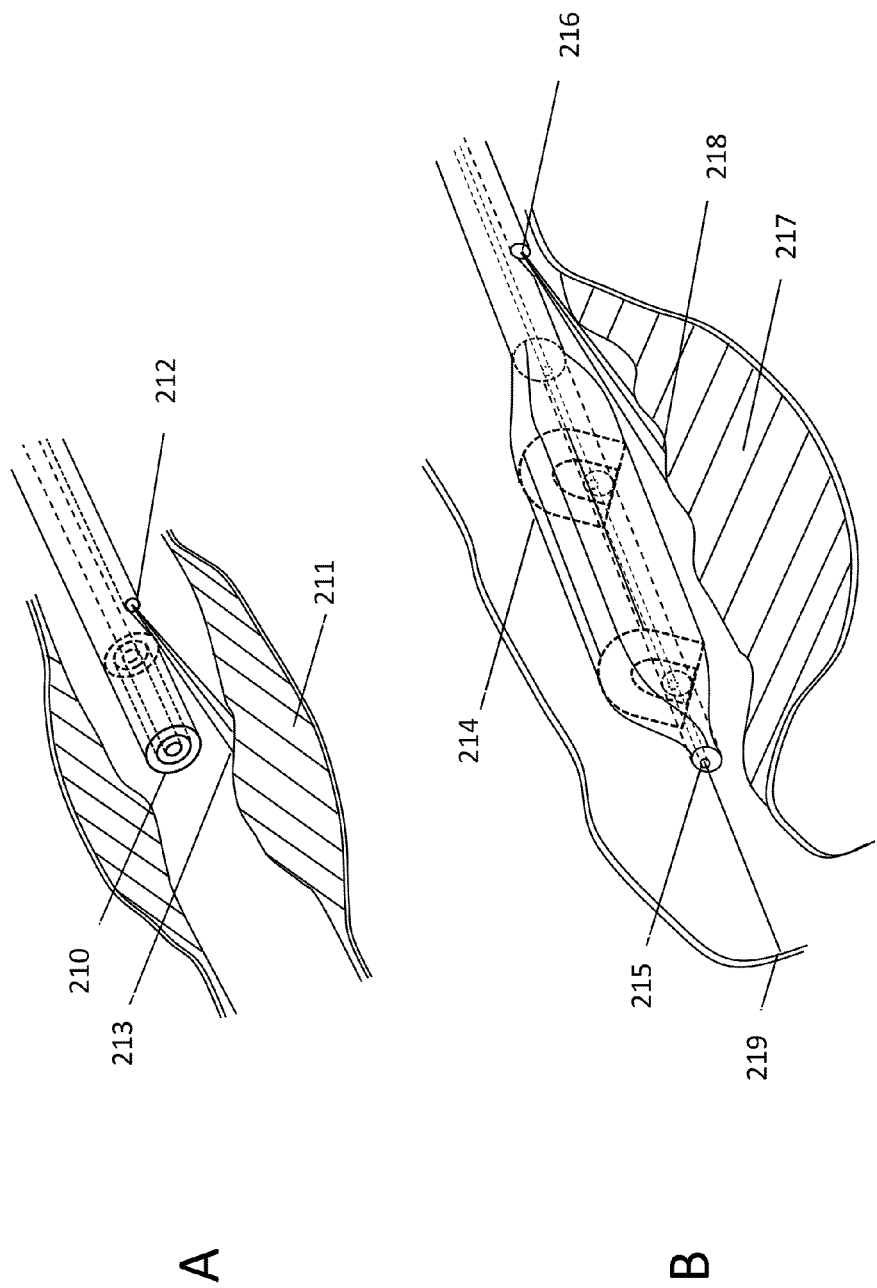
FIG. 17 illustrates a schematic view of examples of infrared thermometry through a view window of fiberoptic cable of flexible tubular device.

FIG. 17 shows a schematic view of examples of infrared thermometry through a view window of a fiberoptic cable of flexible tubular device. FIG. 17A shows distal end 210 of a flexible tubular device inserted into a target area that is surrounded by tumor 211. View window 212 of a fiberoptic cable of said flexible tubular device emits infrared to treatment area 213 of the tumor 211, receives back bounced said infrared light and sends said infrared light to the control module for temperature measurement. The view window 212 also emits visible light to said treatment area 213, receives bounced said visible light back and sends said visible light to the proximal end 8 as shown in FIG. 1 of said flexible tubular device and to the control module for visual display.

FIG. 17B shows distal end 214 of Type A flexible tubular device inserted in close proximity to tumor 218 of a lumen. Fiberoptic view window 215 emits infrared light to normal, untreated area 219 and receives said infrared light back and sends said infrared light to the control module for temperature monitoring of the normal, untreated area 219. Fiberoptic view window 216 emits infrared light to treatment area 218, receives said infrared light back and sends said infrared light to said control module for temperature measurement. Said control module measures temperature of the normal, untreated area 219 and the area under treatment 218 and also calculates differences in temperature between these two areas. The fiberoptic view window 216 also emits visible light to the treatment area 218, receives said visible light back and sends said visible light to the proximal end 8 as shown in FIG. 1 of said flexible tubular device. Visible light carried by said fiberoptic cable can also be sent to the control module for monitor display.

Figure 18:
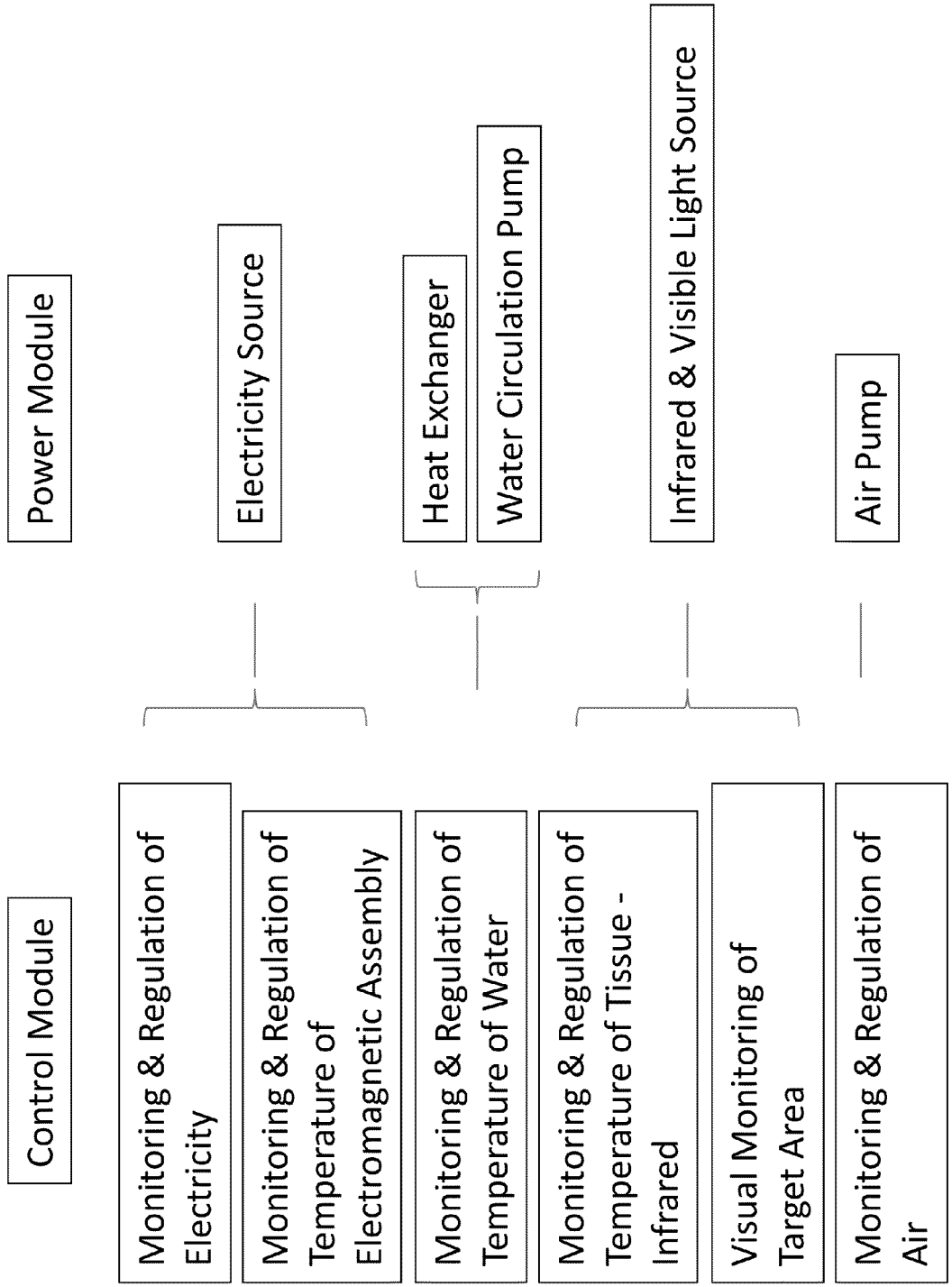
FIG. 18 depicts a schematic explanatory diagram of an example of individual systems of power and control assembly.

FIG. 18 depicts a schematic explanatory diagram of individual systems of both power and control modules for flexible tubular devices. The power module provides electricity to said electromagnetic assembly and resistant temperature detector system, water and said heat exchange unit for said cooling system, infrared and visible light to said fiberoptic system and pressured air for said air balloon of said position stabilization system of said flexible tubular device. The control module is connected to said power module and to said flexible tubular device. The control module provides monitoring and regulation of electricity, temperature of electromagnetic assembly, circulating water of the cooling chamber of distal end, tissue temperature by infrared thermometry and air for said air balloon. In addition, the control module provides visual monitoring of target area by said fiberoptic system.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A thermal apparatus comprising: a flexible tubular device, having a proximal end, a distal end, a flexible tubular portion connecting said proximal and distal ends, and a fiberoptic system, which is provided as one or a plurality of operating devices having one or a plurality of mechanical configurations, and which is configured for insertion into a lumen or a cavity of a body to reach a target area and which provides electromagnetic field in said target area; the distal end, which is provided as one or a plurality of operating devices having one or a plurality of mechanical configurations and which connects to said flexible tubular portion, and which encloses an electromagnetic assembly that receives electric current to generate electromagnetic field; the flexible tubular portion, provided as one or a plurality of operating devices having one or a plurality of mechanical configurations and which carries electrically conductive wires to said electromagnetic assembly of said distal end, one or a plurality of conduits and cables, and which provides navigation of said device; and the fiberoptic system, which is provided as one or a plurality of operating devices having one or a plurality of mechanical configurations and which is made of one or a plurality of high temperature-and electromagnetic-field-tolerant optical materials, and which provides visual assessment and infrared thermometry of areas of a lumen or a cavity of a body, which receive therapy with electromagnetic field;

a transphasic fluid of one or a plurality of solutions, which suspends a plurality of magnetic particles in one or a plurality of concentrations, which is to be administrated to blood vessels through vascular catheter to target blood vessels connected to a target area and which is to be reversibly electromagnetically paired with an electromagnetic assembly of a flexible fiberoptic tubular device of said thermal apparatus inserted into a lumen or a cavity of a body to reach said target area;

the transphasic fluid comprises magnetic particles of different sizes and shapes combined together at varying ratios;

the transphasic fluid is in liquid phase off static electromagnetic field and in gel-like or semi-solid phase on static electromagnetic field;

the gel-like transphasic fluid of magnetic particles introduced to target blood vessels are to get localized in the target blood vessels of the target area and to form internal mold of reversible random lattice structure made of magnetic particles inside said target blood vessels by one or a plurality of static electromagnetic fields generated from direct electric current to said electromagnetic assembly; and the magnetic particles of said gel-like transphasic fluid producing said internal mold of said blood vessels generate heat energy under alternating electromagnetic field, which is to achieve temperature of said target blood vessels and said target area high enough to make tissue of said target blood vessels and said target area die but low enough to avoid damage to normal tissue adjacent to said target blood vessels and said target area over a range of duration.

2. A thermal apparatus comprising: a flexible tubular device, having a proximal end, a distal end, a flexible tubular portion connecting said proximal and distal ends, and a fiberoptic system, which is provided as one or a plurality of operating devices having one or a plurality of mechanical configurations, and which is configured for insertion into a lumen or a cavity of a body to reach a target area and which provides electromagnetic field in said target area; the distal end, which is provided as one or a plurality of operating devices having one or a plurality of mechanical configurations and which connects to said flexible tubular portion, and which encloses an electromagnetic assembly that receives electric current to generate electromagnetic field; the flexible tubular portion, provided as one or a plurality of operating devices having one or a plurality of mechanical configurations and which carries electrically conductive wires to said electromagnetic assembly of said distal end, one or a plurality of conduits and cables, and which provides navigation of said device; and the fiberoptic system, which is provided as one or a plurality of operating devices having one or a plurality of mechanical configurations and which is made of one or a plurality of high temperature-and electromagnetic-field-tolerant optical materials, and which provides visual assessment and infrared thermometry of areas of a lumen or a cavity of a body, which receive therapy with electromagnetic field;

a thermal coil, constructed of one or a plurality of thermal materials and configured as one or a plurality of shapes, sizes and thicknesses, which reaches a target area in a lumen or a cavity by one or a plurality of methods and which generates heat under alternating electromagnetic field produced by the electromagnetic assembly of the flexible fiberoptic tubular device of said thermal apparatus;

the thermal coil is releasably deployed inside said lumen or said cavity and exerts a range of outward radial pressure to an inner wall of said lumen or said cavity;

the thermal coil maintains a helical configuration with its cross-sectional diameter large enough to accommodate the distal end of said flexible tubular device inside of said thermal coil;

the at least one thermal material is magnetic and may be encased to a range of circumference of said material by one or a plurality of thermal barriers along the entire longitudinal length of said material;

the at least one thermal material may be one or a plurality of shape memory alloys;

the thermal barrier comprises one or a plurality of heat resistant polymers;

the thermal coil, under alternating electromagnetic field, generates heat which is to achieve temperature of said target area in contact high enough to make tissue of said target area die but low enough to avoid damage to normal tissue adjacent to said target area over a range of duration; and the thermal coil is removable.

3. A thermal apparatus comprising: a flexible tubular device, having a proximal end, a distal end, a flexible tubular portion connecting said proximal and distal ends, and a fiberoptic system, which is provided as one or a plurality of operating devices having one or a plurality of mechanical configurations, and which is configured for insertion into a lumen or a cavity of a body to reach a target area and which provides electromagnetic field in said target area; the distal end, which is provided as one or a plurality of operating devices having one or a plurality of mechanical configurations and which connects to said flexible tubular portion, and which encloses an electromagnetic assembly that receives electric current to generate electromagnetic field; the flexible tubular portion, provided as one or a plurality of operating devices having one or a plurality of mechanical configurations and which carries electrically conductive wires to said electromagnetic assembly of said distal end, one or a plurality of conduits and cables, and which provides navigation of said device; and the fiberoptic system, which is provided as one or a plurality of operating devices having one or a plurality of mechanical configurations and which is made of one or a plurality of high temperature-and electromagnetic-field-tolerant optical materials, and which provides visual assessment and infrared thermometry of areas of a lumen or a cavity of a body, which receive therapy with electromagnetic field;

a magnetic centrifuge machine, constructed as one or a plurality of operating devices having one or a plurality of mechanical configurations, which removes magnetic particles from blood of a body after completion of thermal treatment with said magnetic particles thermally excited by electromagnetic energy generated by the electromagnetic assembly of the flexible fiberoptic tubular device of said thermal apparatus.

4. A thermal apparatus comprising: a flexible tubular device, having a proximal end, a distal end, a flexible tubular portion connecting said proximal and distal ends, and a fiberoptic system, which is provided as one or a plurality of operating devices having one or a plurality of mechanical configurations, and which is configured for insertion into a lumen or a cavity of a body to reach a target area and which provides electromagnetic field in said target area; the distal end, which is provided as one or a plurality of operating devices having one or a plurality of mechanical configurations and which connects to said flexible tubular portion, and which encloses an electromagnetic assembly that receives electric current to generate electromagnetic field; the flexible tubular portion, provided as one or a plurality of operating devices having one or a plurality of mechanical configurations and which carries electrically conductive wires to said electromagnetic assembly of said distal end, one or a plurality of conduits and cables, and which provides navigation of said device; and the fiberoptic system, which is provided as one or a plurality of operating devices having one or a plurality of mechanical configurations and which is made of one or a plurality of high temperature-and electromagnetic-field-tolerant optical materials, and which provides visual assessment and infrared thermometry of areas of a lumen or a cavity of a body, which receive therapy with electromagnetic field;

an electromagnetic assembly of the flexible fiberoptic tubular device, which is enclosed in a semicircle-tubular distal end of said flexible fiberoptic tubular device and which receives electricity to generate electromagnetic field;

the electromagnetic assembly, constructed with electrically conductive coil and a plurality of magnetic flux controllers, which is provided as one or a plurality of operating devices having one or a plurality of mechanical configurations, and which receives direct electric current to generate static magnetic field in and around said assembly or alternating electric current to generate alternating magnetic field in and around said assembly;

the electrically conductive coil, which is provided as one or a plurality of conductive materials having an open toroid configuration winding up around magnetic flux controllers and which receives electricity to generate one or a plurality of magnetic fields;

the electromagnetic field, which is provided as one or a plurality of energies having an electromagnetic configuration and which is vectorially amplified and shielded by magnetic flux controllers; and the magnetic flux controllers, which is constructed with one or a plurality of ferrites or magnetodielectric materials and is provided in a plurality of numbers and which has one or a plurality of magnetic permeabilities, saturation magnetic flux densities, resistivities and Curie temperatures, and which optimizes electromagnetic field of said electrically conductive coil.

5. A thermal apparatus comprising: a flexible tubular device, having a proximal end, a distal end, a flexible tubular portion connecting said proximal and distal ends, and a fiberoptic system, which is provided as one or a plurality of operating devices having one or a plurality of mechanical configurations, and which is configured for insertion into a lumen or a cavity of a body to reach a target area and which provides electromagnetic field in said target area; the distal end, which is provided as one or a plurality of operating devices having one or a plurality of mechanical configurations and which connects to said flexible tubular portion, and which encloses an electromagnetic assembly that receives electric current to generate electromagnetic field; the flexible tubular portion, provided as one or a plurality of operating devices having one or a plurality of mechanical configurations and which carries electrically conductive wires to said electromagnetic assembly of said distal end, one or a plurality of conduits and cables, and which provides navigation of said device; and the fiberoptic system, which is provided as one or a plurality of operating devices having one or a plurality of mechanical configurations and which is made of one or a plurality of high temperature-and electromagnetic-field-tolerant optical materials, and which provides visual assessment and infrared thermometry of areas of a lumen or a cavity of a body, which receive therapy with electromagnetic field;
one or a plurality of flexible tubular conduits, which axially runs inside a flexible tubular portion of the flexible fiberoptic tubular device connecting a proximal end of said flexible fiberoptic tubular device to the distal end of said flexible fiberoptic tubular device, which is constructed of one or a plurality of heat resistant polymers and which has one or a plurality of configurations, and which conveys water, air, substances, catheter, guidewire, thermal coil and electrically conductive wires from said proximal end or from a power and control assembly of said thermal apparatus to said distal end of said device and which circulates pressured water between said power and control assembly and said distal end for cooling; and
a bending portion of the flexible tubular portion of the flexible fiberoptic tubular device, which is provided as one or a plurality of operating devices having one or a plurality of mechanical configurations and which provides bending for navigation of said flexible fiberoptic tubular device inside a lumen or a cavity of a body by enfolding overlapping spirally wound tubular shaft and stabilization of said flexible tubular portion by spiral ribbon encircling said spirally wound tubular shaft.

6. A thermal apparatus comprising: a flexible tubular device, having a proximal end, a distal end, a flexible tubular portion connecting said proximal and distal ends, and a fiberoptic system, which is provided as one or a plurality of operating devices having one or a plurality of mechanical configurations, and which is configured for insertion into a lumen or a cavity of a body to reach a target area and which provides electromagnetic field in said target area; the distal end, which is provided as one or a plurality of operating devices having one or a plurality of mechanical configurations and which connects to said flexible tubular portion, and which encloses an electromagnetic assembly that receives electric current to generate electromagnetic field; the flexible tubular portion, provided as one or a plurality of operating devices having one or a plurality of mechanical configurations and which carries electrically conductive wires to said electromagnetic assembly of said distal end, one or a plurality of conduits and cables, and which provides navigation of said device; and the fiberoptic system, which is provided as one or a plurality of operating devices having one or a plurality of mechanical configurations and which is made of one or a plurality of high temperature-and electromagnetic-field-tolerant optical materials, and which provides visual assessment and infrared thermometry of areas of a lumen or a cavity of a body, which receive therapy with electromagnetic field;
an infrared fiberoptic system of the flexible fiberoptic tubular device, which is provided as one or a plurality of operating devices having one or a plurality of mechanical configurations, which comprises one or a plurality of infrared optical fibers, one or a plurality of optical lenses, a protective sheath and a control module for infrared thermometry, and which provides infrared thermometry of areas of a lumen or a cavity of a body which receives therapy with electromagnetic field;
the at least one infrared optical fiber, which is provided as an operating device having a range of infrared light transmittance, which axially runs inside the flexible tubular device from the proximal to distal ends, which is separated from the fiberoptic fibers for visual assessment, which comprises high-temperature- and electromagnetic field-tolerant materials and which does not have titanium, chromium, erbium or aluminium;
the high-temperature-tolerant and electromagnetic-field-tolerant materials comprise fluoride glass, zinc selenide, germanium dioxide, or silicon;
the at least one optical lens, which comprises high-temperature-and electromagnetic-field-tolerant germanium dioxide, zinc selenide or silicon; and
the protective sheath, which comprises one or a plurality of heat resistant polymer and which is disposed about said infrared optical fibers, which provides protection of said infrared optical fibers and which shields said infrared optical fibers from the visual assessment fiberoptic fibers disposed in parallel with and located adjacent to said infrared optical fibers.

7. A thermal apparatus comprising: a flexible tubular device, having a proximal end, a distal end, a flexible tubular portion connecting said proximal and distal ends, and a fiberoptic system, which is provided as one or a plurality of operating devices having one or a plurality of mechanical configurations, and which is configured for insertion into a lumen or a cavity of a body to reach a target area and which provides electromagnetic field in said target area; the distal end, which is provided as one or a plurality of operating devices having one or a plurality of mechanical configurations and which connects to said flexible tubular portion, and which encloses an electromagnetic assembly that receives electric current to generate electromagnetic field; the flexible tubular portion, provided as one or a plurality of operating devices having one or a plurality of mechanical configurations and which carries electrically conductive wires to said electromagnetic assembly of said distal end, one or a plurality of conduits and cables, and which provides navigation of said device; and the fiberoptic system, which is provided as one or a plurality of operating devices having one or a plurality of mechanical configurations and which is made of one or a plurality of high temperature-and electromagnetic-field-tolerant optical materials, and which provides visual assessment and infrared thermometry of areas of a lumen or a cavity of a body, which receive therapy with electromagnetic field;
a fiberoptic system for visual assessment of the flexible fiberoptic tubular device, which is provided as one or a plurality of operating devices having one or a plurality of mechanical configurations, which comprises one or a plurality of optical fibers, one or a plurality of optical lenses and a protective sheath, and which provides visual assessment of areas of a lumen or a cavity of a body which receives therapy with electromagnetic field;

the at least one optical fiber, which is provided as an operating device having a range of visible light transmittance, which axially runs inside the flexible tubular device from the proximal to distal ends, which is separated from the infrared optical fibers, which comprises high-temperature- and electromagnetic field-tolerant materials and which does not have titanium, chromium, erbium or aluminium;

the high-temperature-tolerant and electromagnetic-field-tolerant materials comprise silicate glass or mixture of silicon dioxide and germanium dioxide;

the at least one optical lens, which comprises high-temperature-and electromagnetic-field-tolerant silicon dioxide, zinc selenide, germanium dioxide or fused quartz; and the protective sheath, which comprises one or a plurality of heat resistant polymer and which is disposed about said optical fibers, which provides protection of said optical fibers and which shields said optical fibers for visual assessment from the infrared optic fibers disposed in parallel with and located adjacent to said optical fibers for visual assessment.

8. A thermal apparatus comprising: a flexible tubular device, having a proximal end, a distal end, a flexible tubular portion connecting said proximal and distal ends, and a fiberoptic system, which is provided as one or a plurality of operating devices having one or a plurality of mechanical configurations, and which is configured for insertion into a lumen or a cavity of a body to reach a target area and which provides electromagnetic field in said target area; the distal end, which is provided as one or a plurality of operating devices having one or a plurality of mechanical configurations and which connects to said flexible tubular portion, and which encloses an electromagnetic assembly that receives electric current to generate electromagnetic field; the flexible tubular portion, provided as one or a plurality of operating devices having one or a plurality of mechanical configurations and which carries electrically conductive wires to said electromagnetic assembly of said distal end, one or a plurality of conduits and cables, and which provides navigation of said device; and the fiberoptic system, which is provided as one or a plurality of operating devices having one or a plurality of mechanical configurations and which is made of one or a plurality of high temperature-and electromagnetic-field-tolerant optical materials, and which provides visual assessment and infrared thermometry of areas of a lumen or a cavity of a body, which receive therapy with electromagnetic field;

a power and control assembly, which comprises a power module and a control module, the power module, which is provided as one or a plurality of operating devices having one or a plurality of mechanical and electronic configurations, which provides said electrically conductive coils of said flexible fiberoptic tubular device with one or a plurality of direct or alternating electric currents, and which provides said flexible fiberoptic tubular device with water, air, one or a plurality of wavelengths of infrared and visible light and one or a plurality of heat exchange units;

the at least one heat exchange unit provides water circulation to and from said flexible fiberoptic tubular device and receives pressured water from said power module and is regulated for exchange rate, volume and speed of circulating water by said control module; and the control module, which is provided as one or a plurality of operating devices having one or a plurality of mechanical and electronic configurations, and which implements predetermined control of said power module and said flexible fiberoptic tubular device.

9. The thermal apparatus according to claim 3, wherein said centrifuge machine comprises:

a rotating chamber, which is provided as one or a plurality of operating devices having one or a plurality of mechanical configurations, and which receives blood from an intake collection bag, spins blood to separate said magnetic particles in blood from the rest of blood under one or a plurality of static electromagnetic fields surrounding said chamber and sends said blood to an outflow collection bag;

a plurality of fixed permanent magnets or electromagnets, which is provided as one or a plurality of operating devices having one or a plurality of mechanical configurations, and which surrounds said rotating chamber in close proximity and which attracts said magnetic particles to a surface of an inner wall of said rotating chamber;

the electromagnets receive direct electric current to produce static electromagnetic field;

a rotor, which is provided as one or a plurality of operating devices having one or a plurality of mechanical configurations and which receives electricity to rotate said rotating chamber;

collection bags, which is provided as one or a plurality of configurations, and which are connected to said rotating chamber and accommodate blood on its way to and from said rotating chamber;

a blood inflow conduit, which is provided as one or a plurality of configurations, and which receives blood from patient and is connected to said intake collection bag that delivers blood to said rotating chamber;

a blood outflow conduit, which is provided as one or a plurality of configurations, and which receives blood from said outflow collection bag and is connected to a blood vessel of patient and returns blood to patient from said outflow collection bag; and a control module, which is provided as one or a plurality of operating devices having one or a plurality of mechanical and electronic configurations, and which controls operations of said centrifuge machine.

10. A thermal apparatus, comprising: a flexible tubular device, having a proximal end, a distal end, a flexible tubular portion connecting said proximal and distal ends, and a fiberoptic system, which is provided as one or a plurality of operating devices having one or a plurality of mechanical configurations, and which is configured for insertion into a lumen or a cavity of a body to reach a target area and which provides electromagnetic field in said target area; the distal end, which is provided as one or a plurality of operating devices having one or a plurality of mechanical configurations and which connects to said flexible tubular portion, and which encloses an electromagnetic assembly that receives electric current to generate electromagnetic field; the flexible tubular portion, provided as one or a plurality of operating devices having one or a plurality of mechanical configurations and which carries electrically conductive wires to said electromagnetic assembly of said distal end, one or a plurality of conduits and cables, and which provides navigation of said device; and the fiberoptic system, which is provided as one or a plurality of operating devices having one or a plurality of mechanical configurations and which is made of one or a plurality of high temperature-and electromagnetic-field-tolerant optical materials, and which provides visual assessment and infrared thermometry of areas of a lumen or a cavity of a body, which receive therapy with electromagnetic field; wherein a plurality of components of said distal end except for said electromagnetic assembly, electrically conductive coil and wires and resistant temperature detectors, and a plurality of parts of said flexible tubular portion are made of heat resistant polymers without metallic materials, which have a range of structural strength and a range of elasticity;

a closed water cooling system, a position stabilization system, a temperature monitoring system and an enclosure of the semicircle-tubular distal end of said flexible fiberoptic tubular device;

the closed water cooling system comprising a cooling chamber and water conduits, which is provided as one or a plurality of operating devices having one or a plurality of mechanical configurations, and which circulates water around the electromagnetic assembly of the semicircle-tubular distal end of said flexible fiberoptic tubular device between said distal end and one or a plurality of heat exchange units of the power and control assembly;

the cooling chamber, which is provided as one or a plurality of configurations having a space between said electromagnetic assembly and inner wall of an enclosure of said distal end, and which allows directional flow of water for cooling of said electromagnetic assembly;

the position stabilization system comprising an air balloon and an air conduit, which is provided as one or a plurality of operating devices having one or a plurality of mechanical configurations, and which stabilizes position of the electromagnetic assembly of the semicircle-tubular distal end of said flexible fiberoptic tubular device in a lumen or a cavity by one or a plurality of operating techniques having a method of inflation of said air balloon;

the air balloon located on the exterior of said electromagnetic assembly and connected to said power module by said air conduit, which is provided as one or a plurality of operating devices having one or a plurality of mechanical configurations, and which receives air from the power module of said power and control assembly to inflate said air balloon;

the temperature monitoring system comprising one or a plurality of resistant temperature detectors, attached on surface of the electrically conductive wire of the semicircle-tubular distal end of said flexible fiberoptic tubular device, which is provided as one or a plurality of operating devices having one or a plurality of mechanical and electronic configurations, and which transmits information of temperature of said electromagnetic assembly to the control module of said power and control assembly; and the enclosure, which is made of one or a plurality of heat resistant polymers and which has one or a plurality of configurations, and which houses said electromagnetic assembly of the semicircle-tubular distal end of said flexible fiberoptic tubular device for insulation and protection and said cooling chamber.

11. The thermal apparatus according to claim 4, wherein the electrically conductive coil of the semicircle-tubular distal end of said flexible fiberoptic tubular device is insulated and winds up around a plurality of the magnetic flux controllers in the open toroid configuration to produce electromagnetic field.

12. The thermal apparatus according to claim 4, wherein the electromagnetic assembly of the semicircle-tubular distal end of said flexible fiberoptic tubular device generates static electromagnetic field by direct electric current, alternating electromagnetic field by alternating electric current or concurrent direct with alternating electromagnetic fields by continuous direct electric current superimposed by one or a plurality of on-off pulses of alternating electric current, provided by the power and control assembly to said assembly.

13. The thermal apparatus according to claim 5, wherein the bending portion of the flexible tubular portion further comprises:

one or a plurality of spirally wound tubular shafts, constructed as part of an outer wall complex of said flexible tubular portion, which is provided as one or a plurality of operating devices having one or a plurality of cylindrical helix configurations;

that there is an enfolding overlap between two helical edges of said shaft facing each other over one or a plurality of bending radii of said shaft; and that the at least one spirally wound tubular shaft has one or a plurality of pitches between two enfolding helical edges to accommodate a range of bending radii; and one or a plurality of spiral ribbons, constructed as part of said outer wall complex of said flexible tubular portion, which is provided as one or a plurality of operating devices having one or a plurality of helical configurations and which encircles the at least one spirally wound tubular shaft for reversibly fastening and immobilizing said spirally wound tubular shaft;

the fastening and immobilizing said tubular shaft is achieved by shrinking radius of said spiral ribbon by pulling said spiral ribbon toward said proximal end by control knob at the proximal end.

14. The thermal apparatus according to claim 6, wherein infrared light transmitted by said optical fibers is assessed by said control module for temperature of the target area to achieve therapeutic target temperature for a range of length of time or for temperature differences of 6° C. ~8° C. between the untreated area and the target area for a range of length of time, and which is displayed in digitized numerical format for temperature information on said control module.

15. The thermal apparatus according to claim 8, wherein said control module provides:

a temperature monitoring and regulation system of both inflow and outflow of water, which is provided by one or a plurality of operating devices having one or a plurality of mechanical and electronic configurations, and which regulates volume and exchange rate of said water for cooling of said electromagnetic assembly through said heat exchange unit of said power module;

a temperature monitoring and regulation system of said electromagnetic assembly by resistant temperature detectors, which is provided by one or a plurality of operating devices having one or a plurality of mechanical and electronic configurations, and which regulates duration and strength of electric current delivered to said electromagnetic assembly;

infrared thermometry of a target area and non-target area, which is provided by one or a plurality of operating devices having one or a plurality of mechanical and electronic configurations, and which regulates duration and strength of electric current delivered to said electromagnetic assembly;

an electricity monitoring and regulation system for amperage, voltage, frequency and one or a plurality of modes between direct and alternating current, which is provided by one or a plurality of operating devices having one or a plurality of mechanical and electronic configurations, and which controls electrical output of said power module to said electromagnetic assembly; and an air pressure monitoring and regulation system of said air balloon of said position stabilization system, which is provided as one or a plurality of operating devices having mechanical and electronic configurations and which regulates volume and pressure of air to inflate said air balloon.

16. The thermal apparatus according to claim 8, wherein said power and control assembly is shielded by one or a plurality of methods using one or a plurality of materials from electromagnetic field generated by said distal end of said flexible fiberoptic tubular device.

17. A method for the thermal apparatus according to claim 2, wherein said thermal coil is introduced to a target area through a conduit of said flexible fiberoptic tubular device under alternating electromagnetic field in one or a plurality of techniques.

18. A method for the thermal apparatus according to claim 2, wherein said thermal coil is introduced to a target area over said flexible fiberoptic tubular device under alternating electromagnetic field in one or a plurality of techniques, with said thermal coil disposed about the exterior of the distal end of said flexible fiberoptic tubular device.

19. A method for the thermal apparatus according to claim 2, wherein said thermal coil is releasably removed by one or a plurality of methods, following completion of thermal therapy.

20. A method for the thermal apparatus according to claim 2, wherein said thermal coil is left in place at the target area for repeat thermal therapy.

21. A method for the thermal apparatus according to claim 8, wherein said power and control assembly provides said transphasic fluid with one or a plurality of direct electric currents to generate static electromagnetic field to reversibly change the phase of said transphasic fluid from liquid to gel-like or to semi-solid state.

22. A method for the thermal apparatus according to claim 8, wherein said power and control assembly provides said transphasic fluid with one or a plurality of continuous direct electric currents superimposed by one or a plurality of on-off pulses of alternating electric currents, which is to maintain said gel-like or semi-solid phase of said transphasic fluid by static electromagnetic field while producing heat energy from said magnetic materials of said fluid by alternating electromagnetic field.

23. A method for thermal apparatus according to claim 1, wherein intravascular catheter introduced into said one of target blood vessels provides:

rapid bolus infusion of saline to said target blood vessels to flush out blood in said target blood vessels in one or a plurality of techniques, prior to infusion of said transphasic fluid to target blood vessels;

saline of temperature higher than normal body's temperature by a few degrees centigrade infused to said target blood vessels in one or a plurality of techniques, during thermal treatment at a range of rates through said intravascular catheter to said target blood vessels following infusion of full dose of said fluid, which is to prevent localized intravascular coagulation and thrombosis of blood and to prevent loss of heat energy of said magnetic materials under alternating electromagnetic field, infusion of a test dose of said transphasic fluid to said target blood vessels in one or a plurality of techniques, which precedes infusion of a full dose of said transphasic fluid, which is to confirm distribution of said transphasic fluid in said target blood vessels and said target area by one or a plurality of radiologic imaging techniques; and infusion of saline of temperature lower than normal body's temperature by a few degrees centigrade for the cool-down process of said transphasic fluid following thermal therapy to said target blood vessels in one or a plurality of techniques, while said static electromagnetic field is maintained on.

24. A method for thermal apparatus according to claim 9, wherein said magnetic particles delivered to said target blood vessels are removed from blood by one or a plurality of techniques, following completion of the thermal treatment and cool-down process, which uses one or a plurality of separations in magnetic gravitational field.

* * * * *